United States Patent [19]
Mueller et al.

[11] Patent Number: 5,885,833
[45] Date of Patent: Mar. 23, 1999

[54] NUCLEIC ACID CONSTRUCTS FOR THE CELL CYCLE-REGULATED EXPRESSION OF GENES AND THERAPEUTIC METHODS UTILIZING SUCH CONSTRUCTS

[75] Inventors: Rolf Mueller; Joerk Zwicker; Hans-Harald Sedlacek, all of Marburg, Germany

[73] Assignee: Hoechst Aktiengesellschaft, Frankfurt am Main, Germany

[21] Appl. No.: 798,738

[22] Filed: Feb. 13, 1997

[30] Foreign Application Priority Data

Feb. 13, 1996 [DE] Germany ................ 196 05 274.2

[51] Int. Cl.⁶ .................. C12N 5/10; C12N 15/86
[52] U.S. Cl. .................. 435/372; 435/320.1; 536/24.1
[58] Field of Search .................. 435/320.1, 372; 536/24.1

[56] References Cited

FOREIGN PATENT DOCUMENTS 0 464 633 B1  6/1991  European Pat. Off. .

OTHER PUBLICATIONS

Müller, *TIG*, vol. 11, 1995, pp. 173–178.
A. Barbaris et al., "Mutually Exclusive Interaction of the CCAT–Binding Factor and of a Displacement Protein with Overlapping Sequences of a Histone Gene Promoter," Cell 50, (1987), pp. 347–359.
S. Chellappan et al., "The E2F Transcription Factor is a Cellular Target for the R8 Protein," Cell 65, (1991), pp. 1053–1061.
T. Chittanden et al., "The T/E1A–Binding Domain of the Retinoblastoma Product Can Interact Selectively with a Sequence–Specific DNA–Binding Protein," Cell 65, (1991), pp. 1073–1082.
M. Ewen et al., "Molecular Cloning, Chromosamal Mapping, and Expression of the cDNA for p107, a Retinoblastoma Gene Product–Related Protein," Cell 66, (1991), pp. 1155–1164.
K. Holin et al., "A cDNA Encoding a pRB–Binding Protein with Properties of the Transcription Factor E2F," Cell 70, (1992), pp. 337–360.
W. Kaolin et al., Cell, "Expression Cloning of a cDNA Encoding a Retinoblastoma–Binding Protein with E2F–like Properties," Cell 70, (1992), pp. 351–364.
F. Lucibello et al., "Periodic cdc25C transcription is mediated by a novel cell cycle–regulated repressor element (CDE)," The EMBO Journal 14, (1995), pp. 132–142.
E. Lam et al., "HPV16 E7 oncoprotein deregulates B–myb expression: correlation with targeting of p107/E2F complexes," The EMBO Journal 13, (1994), pp. 871–878.
E. Lam et al., "An E2F–binding site mediates cell–cycle regulated repression of mouse B–myb transcription," The EMBO Journal 12, (1993), pp. 2705–2713.
M. Mudryj et al., "A role for the adenovirus inducible E2F transcription factor in a proliferation dependent signal transduction pathway," The EMBO Journal 9, (1990), pp. 2179–2184.

G. Pfeifer et al., "Genomic Sequencing and Methylation Analysis by Ligation Mediated PCR," Science 246, (1989), pp. 810–813.
R. Bernards et al., "Structure and expression of the murine retinoblastoma gene and characterization of its encoded protein," Proc. Natl. Acad. Sci. USA 86, (1989), pp. 6474–6478.
G. Ginsberg et al., "E2F–4 a new member of the E2F transcription factor family, Interacts with p107," Genes & Development 8, (1994), pp. 2665–2679.
R. Baijersbergen et al., "E2F–4, a new member of the E2F gene family, has oncogenic activity and associates with p107 in vivo," Genes & Development B, (1994), pp. 2680–2690.
L. Bandara et al., "Cyclin A and the retinoblastoma gene product complex with a common transcription factor," Nature 352, (1991), pp. 249–251.
Burrows et al., "Vascular Targeting–A New Approach to The Therapy of Solid Tumors," Pharmac. Therp. 64, (1994), pp. 155–174.
Murskami et al., "Identification of Two Enhancer Elements in the Gene Encoding The Type 1 Glucose Transporter from the Mouse Which Are Responsive to Serum, Growth Factor, and Oncogenes," J. Biol. Chem. 267, (1992), pp. 9300–9308.
Bellon et al., "Identification and expression of two forms of the human transforming growth factor B–binding protein endoglin with distinct cytoplasmic regions," Eur. J. Immunol. 23, (1993), pp. 2340–2345.
Ge et al., "Cloning and expression of a cDNA encoding mouse endoglin, in endothelial cell TGF–β ligand," Gene 138, (1984), pp. 201–206.
Plato et al., "Vascular Endothelial Growth Factor and Glioms Anglogenesis: Coordinate Induction of VEGF Receptors, Distribution of VEGF Protein and Possible In Vivo Regulatory Mechanisms," Int. J. Cancer 59, (1994), pp. 520–529.
Sanger et al., "Vascular permeability factor (VPF, VEGF) in turmor biology," Cancer and Matastasis Reviews 12, (1993), pp. 303–324.
Partanen et al., "A Novel Endothalial Cell Surface Receptor Tyrosine Kinase with Extracellular Epidermal Growth Factor Hemology Domains," Mol. and Cell. Biol. 12, (1992), pp. 1696–1707.
Bartley et al., "B61 is a ligand for the ECK receptor protein–tyrosine kinase," Nature 368, (1994), pp. 558–560.
Pandey et al., "Role of B61, the Ligand for the Eck Receptor Tyrosine Kinase, in TNF–o–induced Angiogenesis," Science 268, (1995), pp. 567–569.

(List continued on next page.)

*Primary Examiner*—James Ketter
*Attorney, Agent, or Firm*—Foley & Lardner

[57] ABSTRACT

Nucleic acid constructs comprising an activator sequence, a promoter module, and a structural gene are disclosed. The promoter module comprises a a CHR region and a nucleic acid sequence that binds a protein of the E2F family. These constructs are used in gene therapy, such as the treatment of disorders characterized by excess cell proliferation.

19 Claims, 7 Drawing Sheets

OTHER PUBLICATIONS van der Geer et al., "Receptor Protein–Tyrosine Kinases and Their Signal Transduction Pathways," Ann. Rev. Cell. Biol. 10, (1994), pp. 251–337.

Holzman et al., "The ECK Receptor Tyrosine Kinase Ligand is Induced During Mesodermal Differentiation in P19 Embryonal Carcinoma Cells," 82P, J. Am. Soc. Nephrol. 4, (1993) p. 466.

Holzman et al., "Cloning, Characterization, and Chromosomal Localization of the Human B81 Gene, the ECK Receptor Tyrosine Kinase Ligand," 61P, J. Am. Soc. Nephrol. 4, (1993) p. 486.

Banard et al., "Two Preproendothelin 1 mRNAs Transcribed by Alternative Promoters," J. Clin. Invest. 91, (1993), pp. 1149–1156.

Wilson et al., "A Nonerythroid GATA–Binding Protein is Required for Function of the Human Preproendothelin–1 Promoter in Endothelial Cells," Molecular and Cellular Biology 10, (1990), pp. 4654–4862.

Webb et al., "Cloning and Expression of an Endothelin Receptor Subtype B from Human Prostate that Mediates Contraction," Molecular Pharmacology 47, (1995), pp. 730–737.

Ludwig et al., "Cloning and sequencing of cDNAs encoding the full–length mouse mannose 6–phosphate/insulin–like growth factor II receptor," Gene 142, (1994), pp. 311–312.

Oshima et al., "The Human Cation–independent Mannose 6–Phosphate Receptor," Journal of Biology Chemistry 263, (1988), pp. 2553–2582.

Pohlmann et al., "Cloning of a cDNA encoding the human cation–dependent mannose 6–phosphate–specific receptor," Proc. Natl. Acad, Sci. USA 84, (1987), pp. 5575–5579.

Jahroudi et al., "Endothellal–Cell–Specific Regulation of von Willebrand Factor Gene Expression," Molecular and Cellular Biology 14, (1994), pp. 999–1008.

Ferreira et al., "The role of the 5'–flanking region in the cell–specific transcription of the human von Willebrand factor gene," Biochem. J. 293, (1993), pp. 641–648.

Aird et al., "Human von Willebrand factor gene sequences target expression to a subpopulation of endothelial cells in transgenic mice," Proc. Natl. Acad. Sci. USA 92, (1995), pp. 4567–4571.

Turner et al., "Regulation of Expression of Human IL–1α and IL–1β Genes," Journal of Immunology 143, (1989), pp. 3556–3561.

Fenton et al., "Transcriptional Regulation of the Human Prointerleukin 1β Gene," Journal of Immunology 138, (1987), pp. 3972–3979.

Hiacott et al., "Characterization of a Functional NF–αB Site in the Human Interleukin 1β Promoter, Evidence for a Positive Autoregulatory Loop," Mol. and Cell. Biol. 13, (1993), pp. 6231–6240.

Mori et al., "Transactivation of the Interleukin–1α Gene Promoter by Human T–Cell Leukemia Virus Type 1 Tex in T Cells," Blood 84, (1994), pp. 1688–1689.

Ye et al., "Identification of the promoter region of human interleukin 1 type 1 receptor gene: Multiple initiation sites, high G +C content and constitutive expression," Proc. Natl. Acad. Sci. USA 90, (1993), pp. 2295–2299.

Neish et al., "Endothelial Interferon Regulatory Factor 1 Cooperates with NF–αB as a Transcriptional Activator of Vascular Cell Adhesion Molecule 1," Mol. and Cell. Biol. 15, (1995), pp. 2558–2569.

Ahmad et al., "Cell Typo–specific Transactivation of the VCAM–1 Promoter through an NF–αB Enhancer Motif," Journal of Biological Chemistry 270, (1995), pp. 8976–8983.

Neish et al., "Functional Analysis of the Human Vascular Cell Adhesion Molecule 1 Promoter," J. Exp. Med. 176, (1992), pp. 1583–1593.

Iademarco et al., Characterization of the Promoter for Vascular Cell Adhesion Molecule–1 (VCAM–1) Journal of Biological Chemistry 267, (1992), pp. 16323–16329.

Cybulsky et al., "Gene structure, chromosomal location, and basis for alternative mRNA splicing of the human VCAM[1] gene," Proc. Natl. Acad. Sci. USA 89, (1991), pp. 7859–7863.

Lee et al., "Cloning of the GATA–binding Protein That Regulates Endothelin–1 Gene Expression in Endothelial Cells," Journal of Biological Chemistry 266, (1991), pp. 16188–16192.

Dorfman et al., "Human Transcription Factor GATA–2," J. of Biol. Chem. 267, (1992) pp. 1279–1285.

Minchenka et al., "Hypoxia Regulatory Elements of the Human Vascular Endothelial Growth Factor Gene, " Cellular and Molecular Biology Research 40, (1994), pp. 35–39.

Tischer et al., "The Human Gene for Vascular Endothelial Growth Factor," Journal of Biological Chemistry 266, (1991), pp. 11947–11954.

Mukhopadnyay et al., "Hypoxic induction of human vascular endothelial growth factor expression through c–Src activation," Nature 375, (1995), pp. 577–581.

Bonham et al., "Organization and analysis of the promoter region and 5' non–coding exons of the human c–src proto–oncogene," Oncongene 8, (1993), pp. 1973–1981.

Parker et al., "Isolation of Duplicated Human c–src Genes Located on Chromosomes 1 and 20," Molecular and Cellular Biology 5, (1995), pp. 831–838.

Anderson et al., "Human Cellular src Gene: Nucleotide Sequences and Derived Amino Acid Sequence of the Region Coding for the Carboxy–Terminal Two–thirds of pp. 60 ," Molecular and Cellular Biology 5, (1985). pp. 1122–1129.

Gibbs et al., "Isolation and Structural Mapping of a Human c–src Gene Homolgous to the Transforming Gene (v–src) of Rous Sarcoma Virus," Journal of Virology 53, (1985), pp. 19–24).

Truss et al., "Steroid Hormone Receptors: Interaction with Deoxyribonucleic Acid and Transcription Factors," Endocrine Reviews 14, (1993), pp. 459–479.

Chalepakis et al., "Differential Gene Activation by Gluea-corticoids and Progestine through the Hormone Regulatory Element of Mouse Mammary Tumor Virus," Cell 53, (1988), pp. 371–382.

Cruciani et al., "Antibiotic magainins exert cytolytic activity against transformed cell lines through channel formation," Proc. Natl. Acad. Sci. USA 88, (1991), pp. 3972–3796.

Peck–Miller et al., "Identification of serum components that inhibit the tumoricidal activity of amphiphilic alpha helical peptides," Cancer Chemother Pharmacol 32, (1993), pp. 109–115.

Jarvis et al., "Induction of apoptotic DNA damage and cell death by activation of the sphingomyelin pathway," Proc. Natl. Acad. Sci. USA 91, (1994), pp. 73–77.

Deonsrain et al., "Targeting enzymes for cancer therapy: old enzymes in new roles," Br. J. Cancer 70, (1994), pp. 788–794.

Mullen, "Metabolic Suicide Genes in Gene Therapy," Pharmac. Ther. 63, (1994), pp. 199–207.

Harris et al., "Gene therapy for cancer using tumour–specific prodrug activation," Gene Therapy 1, (1994), pp. 170–175.

Colbere–Garapin et al., "Cloning of the active thymidine kinase gene of herpes simplex virus type 1 in *Escherichia coli* K–12," Proc. Natl. Acad. Sci. USA 76, (1979), pp. 3755–3759.

Vile et al., "Use of Tissue–specific Expression of the Herpes Simplex Virus Thymidine Kinase Gene to Inhibit Growth of Established Murine Melanomas following Direct Intratumoral Injection of DNA," Cancer Research 53, (1993), pp. 3860–3864.

Wagner et al., "Nucleotide sequence of the thymidine kinase gene of herpes simplex virus type 1," Proc. Natl. Acad. Sci. USA 76, (1981), pp. 1441–1445.

Moolten, "Tumor Chemosensitivity Conferred by Inserted Herpes Thymidine Kinase Genes: Paradigm for a Prospective Cancer control Strategy," Cancer Research 46, (1996), pp. 5276–5281.

Moolten et al., "Curability of Tumors Bearing Herpes Thymidine Kinase Genes Transferred by Retroviral Vectors," J. Natl. Cancer Inst. 82, (1990), pp. 297–300.

Huber et al., "Retroviral–mediated gene therapy for the treatment of hepatocellular carcinoma: An innovative approach for cancer therapy," Proc. Natl. Acad. Sci. USA 88, (1991), pp. 8039–8043.

Snoock et al., "Chemotherapy of varicella zoster virus infections," International Journal of Antimicrobial Agents 4, (1994), pp. 211–226.

Michael et al., "Physical characterization of the *Escherichia coli* B gene encoding nitroreductase and its over–expression in *Escherichia coli* K12," FEMS Microbiology Letters 124, (1994), pp. 195–202.

Bryant et al., "Cloning, Nucleotide Sequence, and Expression of the Nitroreductase Gene from *Enterobacter ciosce*," Journal of Biological Chemistry 266, (1991), pp. 4126–4130.

Watanaba et al., "Nucleotide sequence of *Salmonella typhimurium* nitroreductase gene," Nucleic Acids Research 18, (1990), p. 1059.

Jefferson et al., "β–Glucuronidase from *Escherichia coli* as a gene–fusion marker," Proc. Natl. Acad. Sci. USA 83, (1986), pp. 8447–8451.

Schulz et al., "Partial Purification and Characterization of a Luteolin Triglucuronide–Specific βGlucuronidase from Rye Primary Leaves (Secale Careale)," Phytochem. 26, (1987), pp. 833–837.

Bosslet et al., "Molecular and functional characterization of a fusion protein suited for tumour specific prodrug activation," Br. J. Cancer 85, (1992), pp. 234–238.

Oshima et al., "Cloning, sequencing, and expression of cDNA for human β–glucuronidase," Proc. Natl. Acad. Sci. USA 84, (1987), pp. 685–689.

Reynolds et al., "Cloning and Characterization of the Novel Gene for Mast Cell Carboxypeptidase A," J. Clin. Invest. 99, (1992), pp. 273–282.

Yamamoto et al., "Isolation of a cDNA Encoding a Human Serum Marker for Acuta Pancreatitis," Journal of Biology Chemistry 267, (1992), pp. 2575–2581.

Catasus et al., "The Sequence and Conformation of Human Pancreatic Procarboxypeptidase A2," Journal of Biology Chemistry 270, (1995), pp. 6651–6657.

Hamilton et al., "Cloning and Nucleotide Sequence of the *Salmonella typhlmurium* dcp Gene Encoding Dipoptidyl Carboxypeptidase," Journal of Bacteriology 174, (1992), pp. 1626–1630.

Osterman et al., "Primary Structure of Carboxypeptidase T: Delineation of Functionally Relevant Features in Zn–Carboxypeptidase Family," Journal of Protein Chemistry 11, (1992), pp. 561–570.

Rodriques et al., "Development of a Humanized Olsulfide–stabilized Anti–p185——Fα–β–Lactamase Fusion Protein for Activation of a Caphalosporin Doxorubicin Prodrug," Cancer Research 55, (1996), pp. 63–70.

Hussein et al., "Cloning and Sequencing of the Metallothioprotein β–Lactamase II Gene of *Bacillus cereus* 569/H in *Escherichia coli*," Journal of Bacteriology 164, (1986), pp. 223–229.

Coque et al., "Genes for a β–lactamase, a penicillin–binding protein and a transmembrane protein are clustered with the caphamycin biosynthetic genes in Norcardia," The EMBO Journal 12, (1993), pp. 631–639.

Mullen et al., "Transfer of the bacterial gene for cytosine dosminase to mammalian cells confers lethal sensitivity to 5–fluorocytosine: A negative selection system," Proc. Natl. Acad. Sci. USA 89, (1992), pp. 33–37.

Austin et al., "A First Step in the Development of Gene Therapy for Colorectal Carcinoma: Cloning, Sequencing, and Expression of *Escherichia coli* Cytosine Desminase," Molecular Pharmacology 43,(1993), pp. 380–387.

Danielson et al., "Characterization of the *Escherichia coli* codBA operon encoding cytosine permase and cytosine deaminase," Molecular Microbiology 6, (1992), pp. 1335–1344.

Erzurum et al., "Protection of human endothellal cells from oxidant injury by adenovirus–mediated transfer of the human catalase cDNA," Nucleic Acids Research 21, (1993), pp. 1607–1612.

Gum et al., "Molecular Cloning of Complementary DNAs Encoding Alkaline Phosphatase in Human Colon Cancer Cells," Cancer Research 50, (1990), pp. 1085–1091.

Sharieff et al., "Molecular Genetics: Gene Identifi.," Am. J. Hum. Den. 49, (1991), p. 412.

Song et al., "Cloning and characterization of a human protein phosphatase 1–encoding cDNA," Gene 129, 1993, 291–295.

Tailor et al., "Nucleotide sequence of human prostatic acid phosphatase determined from a full–length cDNA clone" Nucleic Acids Research 18, (1990), p. 4826.

A. Cassady et al., "Isolation and characterization of the genes encoding mouse and human type–5 acid phosphatase," Gene 130, (1993), pp. 201–207.

Kim et al., "A New Gene with Sequence and Structural Similarity to the Gene Encoding Human Lysyl Oxidase," The Journal of Biology Chemistry 270, (1995), pp. 7176–7182.

Fukui et al., "Molecular Cloning and Chromosomal Localization of Human Gene Encoding D–Amino–acid Oxidase," The Journal of Biological Chemistry 287, (1992), pp. 18631–18638.

Chada et al., "Isolation and Chromosomal Localization of the Human Glutathione Peroxidase Gene," Genomics 8, (1990), pp. 268–271.

Ishida et al., "Nucleotide sequence of a human gene for glutathione peroxidase," Nucleic Acids Research 15, (1997), p. 10051.

Tan et al., "Molecular Cloning of the Human Eosinophil Peroxidase," J. Exp. Med. 169, (1989), pp. 1757–1769.

Sakernaki et al., "Molelcular Cloning and Characterization of a Chromosomal Gene for Human Eosinophil Peroxidase," Journal of Biological Chemistry 264, (1989), pp. 16828–16838.

Kimura et al., "Human thyroid peroxidase: Complete cDNA and protein sequence, chromosome mapping, and identification of two alternately spliced mRNAs," Proc. Natl. Acad. Sci. USA 84, (1987), pp. 5555–5559.

Rischmann et al., "Reshaping human antibodies for therapy," Nature 332, (1988), pp. 323–327.

Mountford et al., "Internal ribosome entry sites and dicistronic RNAs in mammalion transgenesis," TIG 11, (1995), pp. 179–184.

Kaufman et al., "Improved vectors for stable expression of foreign genes in mammallan cells by use of the untranslated leader sequence from EMC virus," Nucleic Acids Res. 19, (1991), pp. 4485–4490.

Morgan et al., "Retroviral vectors containing putative internal ribosome entry sites: development of a polycistronic gene transfer system and applications to human gene therapy," Nucleic Acids Res. 20, (1992), pp. 1293–1299.

Dirks et al., "Dicistronic transcription units for gene expression in mammalian cells," Gene 128, (1993), pp. 247–249.

Palletier et al., "Internal initiation of transistion of eukaryotic mRNA directed by a sequence derived from poliovirus RNA," Nature 334, (1988), pp. 320–325.

Sugimoto et al., "Efficient Expression of Drug–selectable Genes in Retroviral Vectors Under Control of an Internal Ribosome Entry Site," Bio/Technology 12, (1994), pp. 694–698.

Brown, "Synthetic Peptides and Purified Antigens as Vaccines," International Journal of Technology Assessment Health Care 10, (1994), pp. 161–166.

Ellis, "Vaccine Development: Progression From Target Antigen to Product," Adv. Exp. Med. Biol. 327, (1992), pp. 263–271.

Arnon et al., "Structural basis of antigenic specificity and design of new vaccines," Faseb J. 6, (1992), pp. 3265–3273.

Fynan et al., "DNA Vaccines: A Novel Approach to Immunization," Int. J. Immunopharm. 17, (1995), pp. 79–83.

Donnelly et al., "Immunization with Polynucleotides A Novel Approach to Vaccination," The Immunologist 2, (1994), pp. 20–26.

Ewon et al., "Molecular Cloning, Chromosomal Mapping, and Expression of the cDNA for p107, a Retinoblastoma Gene Product–Related Protein," Cell 68, (1991), pp. 1155–1164.

Luciballo et al., "Periodic cdc25C transcription is mediated by a novel cell cycle–regulated repressor element (CDE)," The EMBO Journal 14, (1995), pp. 132–142.

Fig. 4

| | | CDE | | CHR | | |
|---|---|---|---|---|---|---|
| cdc25C | -20 | GGCT | GGCGG AAGGT | TTGAA | TGG | +1 |
| cdc2 | -26 | TTAG | CGCGG TGAGT | TTGAA | ACT | -5 |
| Cyclin A | -39 | TAGT | CGCGG GATAC | TTGAA | CTG | -18 |
| B-Myb | -50 | ACTT | GGCGG GAGAT | AGGAA | AGT | -29 |
| | | E2F | | | | |

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

C T T G G C G G G                                                                  9

( 2 ) INFORMATION FOR SEQ ID NO:2:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

T T T C G C G C C                                                                  9

( 2 ) INFORMATION FOR SEQ ID NO:3:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear (xi) SEQUENCE DESCRIPTION: SEQ ID NO:3:

TTTCGCGGC 9

(2) INFORMATION FOR SEQ ID NO:4:

(i) SEQUENCE CHARACTERISTICS:
(A) LENGTH: 7 base pairs
(B) TYPE: nucleic acid
(C) STRANDEDNESS: single
(D) TOPOLOGY: linear (xi) SEQUENCE DESCRIPTION: SEQ ID NO:4:

TAGGAAA 7

(2) INFORMATION FOR SEQ ID NO:5:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:5:

CTTGGCGGGA GATAGGAAAG T 21

(2) INFORMATION FOR SEQ ID NO:6:

(i) SEQUENCE CHARACTERISTICS:
(A) LENGTH: 42 base pairs
(B) TYPE: nucleic acid
(C) STRANDEDNESS: single
(D) TOPOLOGY: linear (xi) SEQUENCE DESCRIPTION: SEQ ID NO:6:

GGCGCCGACG CACTTGGCGG GAGATAGGAA AGTGGTTCTG TG 42

(2) INFORMATION FOR SEQ ID NO:7:

(i) SEQUENCE CHARACTERISTICS:
(A) LENGTH: 42 base pairs
(B) TYPE: nucleic acid
(C) STRANDEDNESS: single
(D) TOPOLOGY: linear (xi) SEQUENCE DESCRIPTION: SEQ ID NO:7:

GGCGCCGACG CACTTGGCTG GAGATAGGAA AGTGGTTCTG TG 42

(2) INFORMATION FOR SEQ ID NO:8:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:8:

GATCGACTAG TTTCGCGCCC TTTCTACTAG 30

(2) INFORMATION FOR SEQ ID NO:9:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:9:

GATCCTCTCA CCTGCTGCTA G 21

( 2 ) INFORMATION FOR SEQ ID NO:10:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

TCAGGACTCA GGCTGCT 17

( 2 ) INFORMATION FOR SEQ ID NO:11:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

CGAGCCGCTC CGGGCCCAG G 21

( 2 ) INFORMATION FOR SEQ ID NO:12:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

GGCCCCAGGC GGTGCTCTCA GGCG 24

( 2 ) INFORMATION FOR SEQ ID NO:13:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

CTTGGCGGGA GATAGGAAA 19

( 2 ) INFORMATION FOR SEQ ID NO:14:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

GACACCCCTG CACCAGAAGT ATC 23

( 2 ) INFORMATION FOR SEQ ID NO:15:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

GGCTGGACTT CAGGCGGCT 19

(2) INFORMATION FOR SEQ ID NO:16:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:16:

GGCTGGCGGA AGGTTTGAAT GG    22

(2) INFORMATION FOR SEQ ID NO:17:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:17:

TTAGCGCGGT GAGTTTGAAA CT    22

(2) INFORMATION FOR SEQ ID NO:18:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:18:

TAGTCGCGGG ATACTTGAAC TG    22

(2) INFORMATION FOR SEQ ID NO:19:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:19:

ACTTGGCGGG AGATAGGAAA GT    22

(2) INFORMATION FOR SEQ ID NO:20:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (xi) SEQUENCE DESCRIPTION: SEQ ID NO:20:

CTTGGCGGGA G    11

NUCLEIC ACID CONSTRUCTS FOR THE CELL CYCLE-REGULATED EXPRESSION OF GENES AND THERAPEUTIC METHODS UTILIZING SUCH CONSTRUCTS

BACKGROUND OF THE INVENTION

The transcription factor E2F was identified as a sequence-specific DNA binding protein complex required for the adenovirus E1A dependent transcription of the E2 gene, and as a differentiation-regulated transcription factor (also termed DRTF-1) in embryonal carcinoma cells. It is now clear that E2F plays a predominant role in the regulation of genes in $G_1$ and S. These genes include known regulators of cell proliferation such as c-myc, B-myb, E2F-1 and RB, as well as a number of genes encoding enzymes associated with DNA synthesis, like Dihydrofolate Reductase (DHFR) and Thymidine Kinase (TK). In its simplest transcriptionally active form the transcription factor E2F is a heterodimeric protein composed of one member of the E2F family, which currently consists of 5 distinct gene products (E2F-1 to E2F-5) of which E2F-1 is the factor analysed in greatest detail at present, and one member of the DP family. Three distinct DP genes and their products have been identified, but the most detailed analyses have been performed with DP-1. The heterodimerisation of E2F family members with DP-1 is synergistic, with respect to both DNA binding and E2F-site dependent transactivation. Apart from such dimeric molecules, frequently referred to as "free E2F", higher order complexes exist in the cell, and the formation of the different complexes is dictated by the cell cycle.

In mammalian cells the heterodimeric E2F/DP transcription factors frequently act as repressors in $G_0$/early $G_1$ owing to their association with pocket proteins of the pRb family. In late $G_1$, the pocket proteins become hyperphosphorylated and dissociate from the complex with E2F/DP, leading to the derepression of E2F-regulated genes. Several genes expressed in late $G_1$/early S, including B-myb, DHFR and E2F-1, have been shown to be repressed through an E2F-mediated mechanism in $G_0/G_1$ and to be derepressed in late $G_1$. The E2F molecules include activating dimeric complexes such as, for example, E2F1-DP1 and trimeric E2F complexes such as, for example, E2F1-DP1-pRb [Bandara et al., Nature, 252, 249 (1991); Chellappan et al., Cell 65, 1053 (1991); Chittenden et al., Cell 65, 1073 (1991); Helin et al., Cell 70, 337 (1992); Kaelin et al., Cell 70, 351 (1992)]. The complexes E2F4-DP1 and E2F4-DP1-p107 have, for example, been described by Beijersbergen et al., Genes Dev. 8, 2680 (1994) and Ginsberg et al., Genes Dev. 8, 2665 (1994).

A property common to transcription factors, to which the E2F molecules belong, is that there is a relation between the expression of genes and the state in which the cell is. There is very little transcription of genes in quiescent cells, whereas transcription is increased in dividing cells. In an experiment with cultivated cells it is possible to stimulate expression by adding serum, preferably fetal calf serum, to quiescent cells.

Cells multiply by cell division, with the genome of the cell being replicated before mitosis. Non-dividing, quiescent cells are in a phase referred to as G0. Alternatively, non-dividing, quiescent cells are inhibited and cannot progress beyond the G1 stage ("G1 block"). When cell division starts, the cells are released from the G0 phase or the G1 block. The G1 phase is a phase which is normally of relatively long duration. The DNA content of the cell is in the diploid state in the G0 and G1 phases. The G1 phase is followed by the S phase in which DNA synthesis takes place and in which the genome is duplicated. This is followed by the second G phase, G2, in which the cell is in the tetraploid state. Mitosis then takes place, and the cell reaches a G1 or G0 state.

The B-myb gene is involved in cell division. Transcription of the B-myb gene increases (for example in mouse fibroblasts) in the late G1 phase of the cell cycle and is most pronounced in the S phase (Lam et al., EMBO J. 12, 2705 (1993)). The nucleotide sequence CTTGGCGGGAG is a constituent of the promoter sequence of the B-myb gene and is involved in the repression of the gene in the G0 and early G1 phases (Lam et al., EMBO J. 12, 2705 (1993)). TTTCGCGC is a constituent of the E2a adenovirus promoter and represents an activating E2F binding site (Mudryj et al., EMBO J. 9, 2179 (1990)).

SUMMARY OF THE INVENTION

It has now been found within the scope of the present invention that a certain region from the promoter sequence of the B-myb gene is able to control expression of a gene which is part of a nucleic acid construct according to the invention. This region, when used in a promoter module (b) according to the invention, is involved in the regulation of a gene located downstream from the promoter, during the G0 and early G1 phases of the cell cycle.

In one embodiment, the invention comprises a nucleic acid construct comprising:
 (a) an activator sequence;
 (b) a promoter module comprising
  (i) a nucleotide sequence which binds a protein of the E2F family; and
  (ii) a nucleotide sequence that is a cell cycle homology region (CHR); and
 (c) a structural gene.

In another embodiment, the invention relates to such a construct, wherein element (a) is upstream of element (b), which is upstream of element (c), and wherein said sequence that binds to a E2F protein is located upstream of said cell cycle homology region. In yet another embodiment, the invention includes such a nucleic acid construct wherein said structural gene encodes a protein that is expressed in a cell cycle-dependent fashion.

In yet another embodiment, the invention relates to such a nucleic acid construct, wherein said nucleotide sequence which binds a protein of the E2F family comprises at least one nucleotide sequence which is selected from the group consisting of CTTGGCGGG (SEQ ID NO:1), TTTCGCGCC (SEQ ID NO:2) and TTTCGCGGC (SEQ ID NO:3). In a futher embodiment of the invention, in the construct the CHR region comprises the nucleotide sequence TAGGAAA (SEQ ID NO:4).

In still another embodiment, the invention relates to a nucleic acid construct as described above, wherein said promoter module (b) comprises the sequence CTTGGCGG-GAGATAGGAAA (SEQ ID NO: 13).

In a further embodiment, the invention relates to a nucleic acid construct as described above, wherein said promoter module (b) interacts with said activator sequence (a), and wherein said interaction affects expression of said gene (c).

In other embodiments, the invention includes a nucleic acid construct, wherein said activator sequence is cell-specific, metabolic specific, or virus-specific.

In another embodiment, the invention relates to a nucleic acid construct as described above, wherein said nucleic acid is DNA.

The invention also relates to a vector comprising any of the above-described nucleic acid constructs. Such a vector may be a plasmid vector or a viral vector.

In other embodiments, the invention relates to a nucleic acid construct as described above, wherein said gene (c) encodes a substance which is selected from the group consisting of a cytokine, a growth factor, a cytokine receptor, a growth factor receptor, a protein having an antiproliferative effect, a protein having a cytostatic effect, an antibody, an antibody fragment, an angiogenesis inhibitor, a coagulation factor and an anticoagulant.

In still a further embodiment, the invention relates to a nucleic acid construct as described above, wherein said activator sequence (a) is from a promoter that is activated in a cell selected from the group of consisting of an endothelial cell, a smooth muscle cell, a macrophage, a lymphocyte, a leukemia cell, a tumor cell and a glial cell.

In a further embodiment, the invention relates to a nucleic acid construct as described above, wherein said activator sequence (a) is a promoter or enhancer sequence from a virus, wherein said virus is selected from the group consisting of the viruses HBV, HCV, HSV, HPV, EBV, HTLV, CMV, SV40 or HIV.

In another embodiment, the invention relates to a nucleic acid construct as described above, wherein said gene (c) encodes an enzyme which cleaves a precursor of a pharmaceutical to produce a pharmaceutical.

The invention also relates to an isolated cell comprising a nucleic acid construct according to the invention.

The invention also relates to a therapeutic method for treatment of a disease characterized by excess cell proliferation, comprising administration of a therapeutically effective amount of a construct according to the invention to a patient in need of such treatment. In one embodiment, the disease treated is cancer.

BRIEF DESCRIPTION OF THE DRAWINGS

FIG. 3A shows cell cycle analysis of NIH3T3 cells synchronized in G0 by withdrawal of serum and stimulated with 10% FCS. Cells were stained with Hoechst 33258 to detect DNA and analyzed by FACS (Lucibello et al., EMBO J. 14, 132 (1995)).

FIG. 3B shows expression of B-myb mRNA during the cell cycle, measured by RT-PCR. Isolation of the RNA and the RT-PCR were carried out as described by Lucibello et al., EMBO J. 14, 132 (1995). The region of the B-myb cDNA from position +1630 to +2228 was amplified using the following primers: (SEQ ID NO: 14) 5'-GACACCC CTG-CACCAGAAGTATC and (SEQ ID NO: 15) 5'-GGCTGGACTTCAGGCGGCT. GPDH served as control.

Figure 3A:
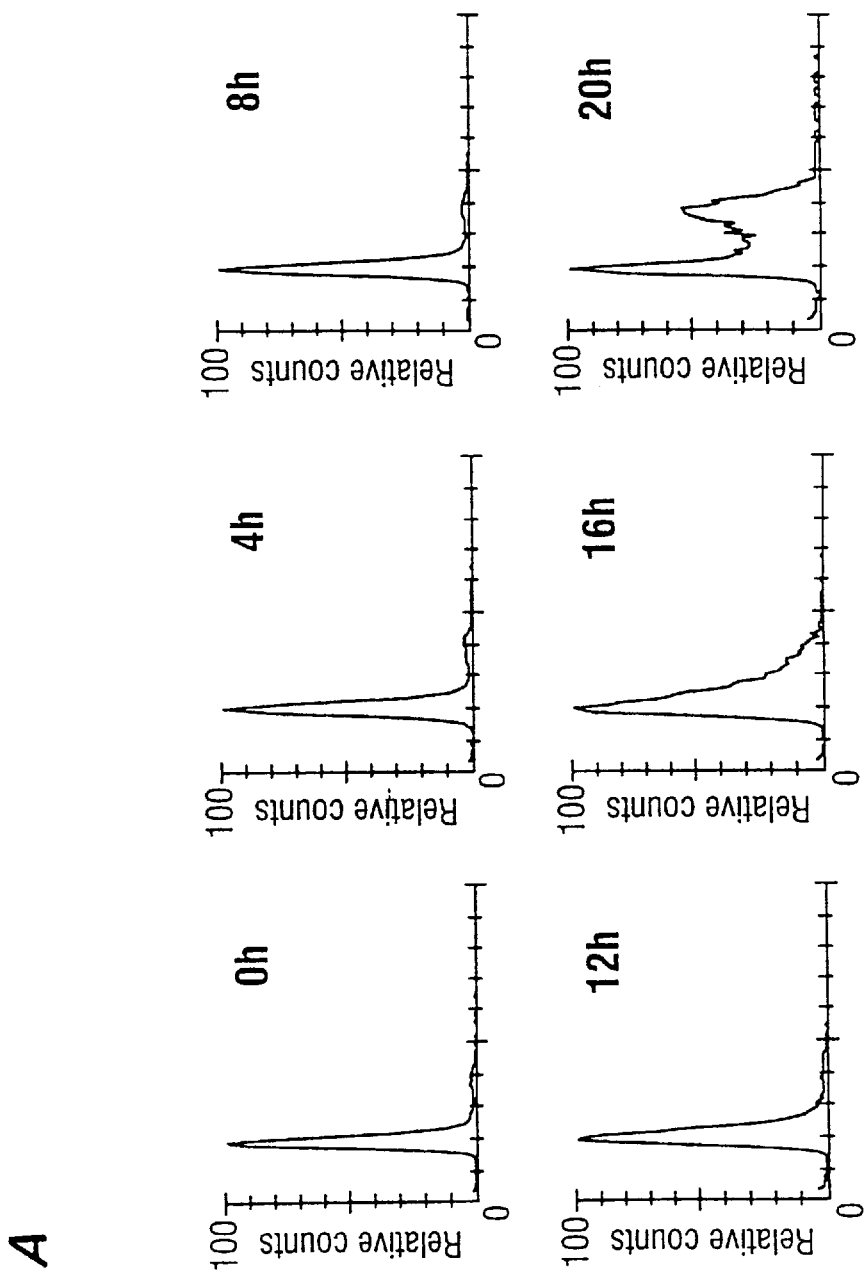
FIGS. 3A and 3B show kinetics of B-myb mRNA expression and occupation of the E2F binding site in the cell.
Figure 3B:
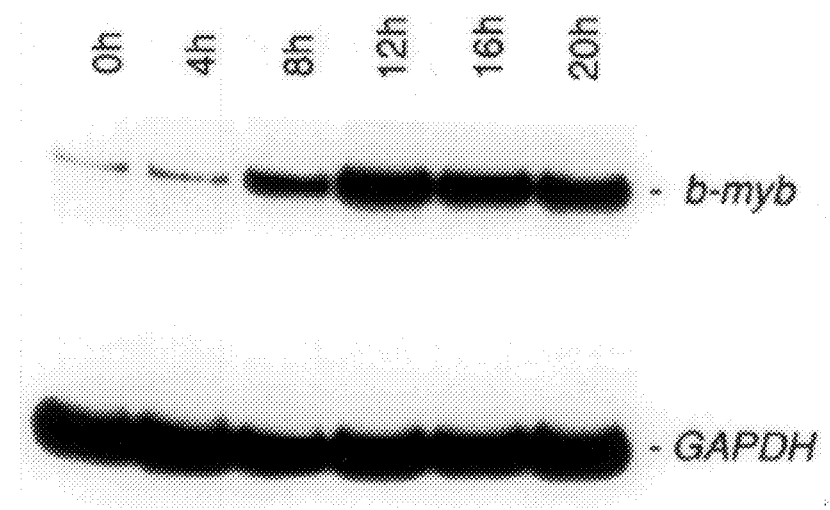
Figure 3C:
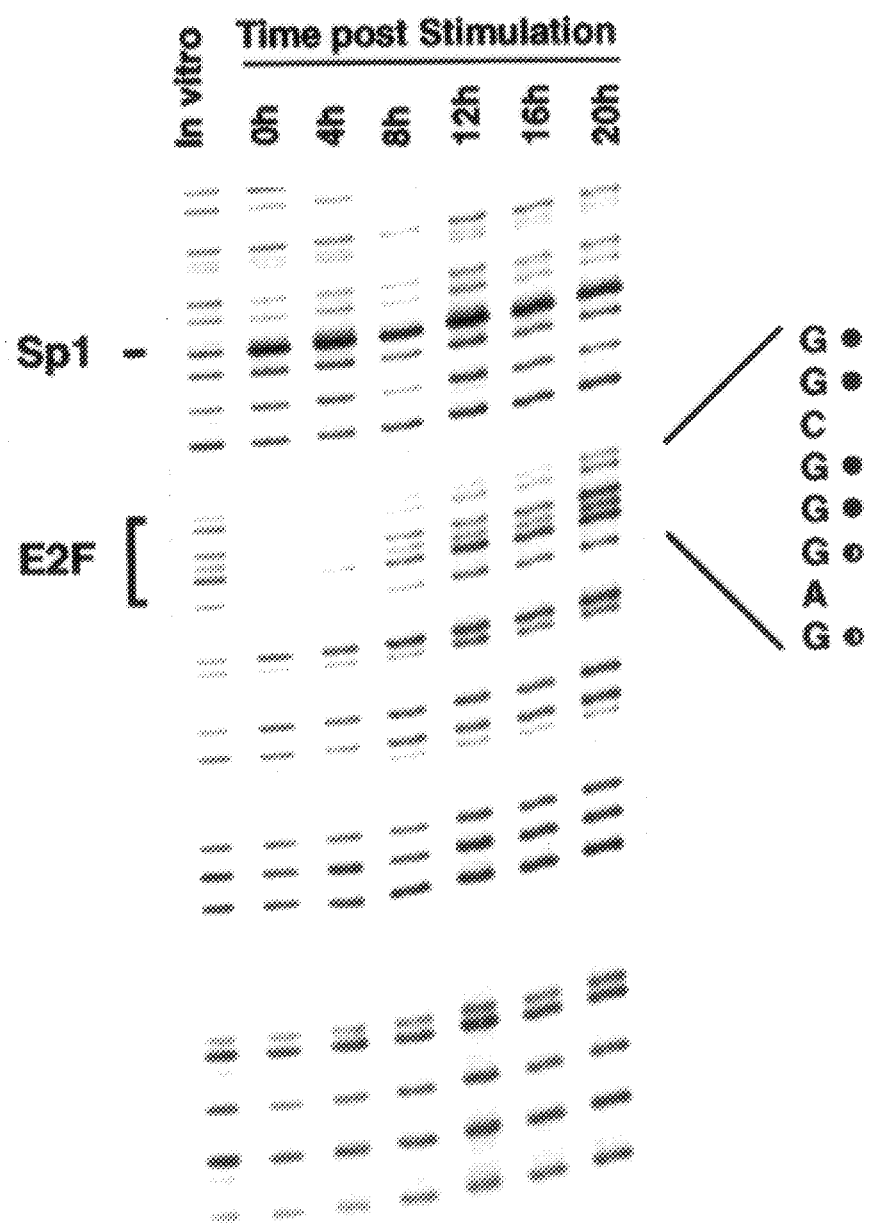
FIG. 3C shows Genomic DMS footprinting (Lucibello et al., EMBO J. 14, 132 (1995) and Pfeiffer et al., Science 256, 810 (1989)) of the B-myb core promoter region in various cell cycle progression stages. The E2F binding site and a potential Sp1 binding site are marked. Filled circles: pronounced protection (>80%, according to phosphor imaging analysis); half-filled circles: partial protection (≈50%).

Analysis of FIGS. 3A, 3B and 3C was carried out with identical cell populations.

FIG. 4 shows comparison of the proximal promoter sequences of cdc25C, cyclin A, cdc2 and B-myb genes (SEQ ID NOS: 16, 18, 17, and 19, respectfully). Position data are taken from the literature (Zwicker et al., EMBO J. 14, 132 (1995)) and relate to the main starting point in each case (B-myb, Lam et al., EMBO J. 12, 2705 (1993)).

Figure 5:
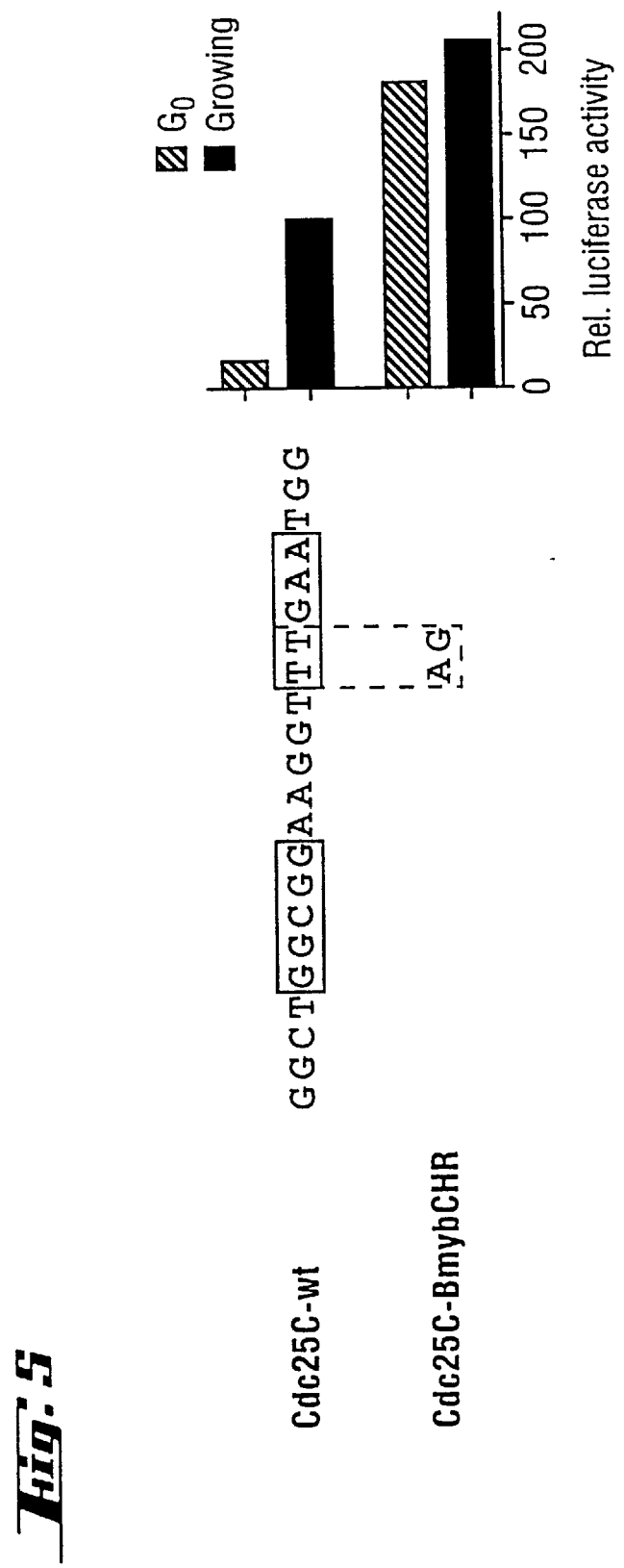

FIG. 5 shows analysis of cdc25C-promoter-luciferase reporter constructs in quiescent (G0) and growing NIH3T3 cells. The wild-type C290 construct (top of figure, Zwicker et al., 1995) was mutated in the CHR region (bottom of figure, bases underlined) to produce a B-myb CHR (Cdc25C-BmybCHR). Analysis was carried out as described in Lucibello et al., EMBO J. 14, 132 (1995) and Zwicker et al., EMBO J. 14, 4514 (1995).

DETAILED DESCRIPTION OF THE INVENTION

It has now been found within the scope of the present invention that the B-myb promoter comprises a high-affinity E2F protein binding site and that the binding of E2F protein molecules to this nucleotide sequence (in particular CTTGGCGGG) in vivo, is surprisingly confined to the G0 and early G1 phases and is undetectable in the S, G2 and M phase (i.e. when the transcription of the B-myb gene is most is pronounced). This is in contrast to the biochemical (in vitro) binding data of Lam et al, EMBO-J. 12, 2705 (1993)) Lam, et al. had reported that E2F complexes bind to the B-myb promoter in the G0 and in the S phase.

It was furthermore not predictable that another binding region is necessary for effective repression of a structural gene in a construct according to the invention. Cyclin A, cdc2 and cdc25C exemplify a group of cell cycle genes whose transcription is up-regulated later than that of B-myb, i.e. in S-phase (cyclin A, cdc2) and $G_2$ (cdc25C) (for a review see Müller, Trends Genet. 11, 173 (1995)). For all three promoters, repression of upstream activators via the "cell cycle-dependent element" (CDE) has been established as the major regulatory mechanism (Lucibello et al., EMBO J. 14, 132 (1995), Zwicker et al., Nucl. Acids Res. 23, 3822 (1995)). In addition, repression of the cyclin A, cdc2 and cdc25C promoters is also dependent on a contiguous element, "cell cycle genes homology region" (CHR) (Zwicker et al., EMBO J. 14, 4514 (1995), hereby incorporated by reference). As shown by genomic footprinting, both elements are bound by the repressor proteins in a periodic fashion, the CDE in the major groove and the CHR in the minor groove. As used in this specification, a "CHR region" is used to mean the nucleotide sequence TAGGAAA (SEQ ID NO:4).

The skilled artisan will recognize that at least one member of the CHF family of proteins is known to bind to the CHR region (TAGGAAA, SEQ ID NO: 4). In this regard, the invention comprises a promoter module that comprises such a CHR region.

It has now been found within the scope of the present invention that there exists a significant homology between the CHR in the cyclin A, cdc2 and cdc25C and the region immediately downstream from the E2F site in the B-myb promoter and that the E2F-mediated repression of B-myb is also dependent on a CHR-like downstream element. The repressor protein for B-myb-CHR is related to but distinct from the factors interacting with the CHR of cdc25C, indicating that both E2F- and CDE-mediated repression is dependent on promoter-specific corepressors. The CHR region is located downstream from the E2F binding site in a construct according to the invention.

Since at the time of transcription of the B-myb gene no binding of the E2F protein to the nucleotide sequence (SEQ ID NO:20) CTTGGCGGGAG was found, the E2F dimers present in the cell play no evident part in the cell cycle regulation of the B-myb gene transcription. Thus the E2F-mediated repression in the $G_0$ and $G_1$ phases is the crucial mechanism in the regulation of B-myb expression.

A nucleic acid construct according to the invention comprises the following components:
(a) an activator sequence whose function is cell-specific or virus-specific or metabolic specific activation of basal transcription;
(b) a promoter module which comprises (1) a first nucleotide sequence which binds a protein of the E2F family and (2) a second nucleotide sequence downstream from the E2F binding site which is a CHR region;
c) a structural gene which encodes a substance which is expressed in a cell-specific, cell cycle-dependent manner, or which is expressed in a virus-specific, cell-cycle dependent manner or which is expressed in a metabolic-specific, cell-cycle dependent manner.

In an another embodiment, the promoter module (b) comprises a transcription-initiating sequence. The arrangement of the nucleic acid constucts according to the invention can be depicted diagrammatically as follows:

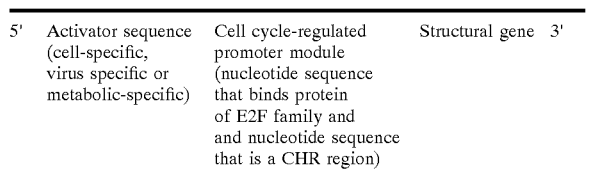

In one embodiment, a nucleic acid construct according to the invention preferably consists of DNA. The term "nucleic acid construct," as used herein, means an artificial nucleic acid structure which can be transcribed in the target cells. Such a construct may be inserted into a vector. In other embodiments, plasmid vectors or viral vectors may be used. A nucleic acid construct according to the invention does not occur in nature in the arrangement contemplated by the present invention. In other words, the gene (c) of the nucleic acid construct is not naturally combined with the activator sequence (a) and the promoter module (b).

A nucleic acid construct according to the invention makes it possible for a gene (c) to undergo both cell- and cell cycle-specific expression, or virus- and cell cycle-specific expression or metabolic- and cell cycle specific expression. In one embodiment, gene (c) is a gene which codes for a pharmacologically active substance. In another embodiment, (c) is a gene encoding an enzyme which cleaves an inactive precursor of a pharmaceutical into an active pharmaceutical ("prodrug" into drug). Examples of such pharmaceutical precursor to pharmaceuticals are described by Hay et al., Drugs of the Future 21, 917, (1996); and Sedlacek et al. Contributions to Oncology No. 43, Karger 1992, both of which are hereby incorporated by reference.

A. Activator Sequence

Component (a), the "activator sequence," means a nucleotide sequence which is part of a gene and to which regulatory proteins, so-called transcription factors, are able to bind and, as a result of that binding activate transcription of the structural gene which is located downstream. The activator sequence can be a promoter or enhancer or can be isolated from one of these types of sequences. The regions referred to as "downstream" sequences are those located in the direction of transcription, whereas sequences arranged in the opposite direction are referred to as "upstream" sequences.

In one embodiment, the activator sequence (a) in the nucleic acid constructs according to the invention is cell-specific or virus-specific or metabolic specific. As used in this specification, "cell-specific" means that the activator sequence is selected from a gene coding for a protein that is specifically expressed in a given cell, and "virus-specific" means that the activator sequence is selected from a viral gene; metabolic specific means, that the activator sequence is selected from a gene, coding for a protein, that is specifically expressed under defined metabolic conditions. Thus in another embodiment, the nucleic acid constructs according to the invention have an activating sequence (a) which is selected from the group of promoters or enhancers which activate transcription in endothelial cells, smooth muscle cells, hemopoietic cells, lymphocytes, macrophages, tumor cells, leukemia cells or glial cells, or from promoter sequences or enhancer sequences of the viruses HBV, HCV, HSV, HPV, EBV, HTLV or HIV. Examples of cell-specific activator sequences, virus-specific sequences and metabolic specific sequences are described below.

B. Promoter Module

The protein transcription factors of the E2F family bind to the promoter module which is used according to the invention and is located downstream of the activating sequence.

In one embodiment, the promoter module (b) comprises a nucleotide sequence which, binds at least one protein of the E2F family. This sequence may be selected from the following nucleotide sequences: CTTGGCGGG (SEQ ID NO:1) (E2F binding site of the B-myb-gene) or a functionally similar (analogous) sequence such as, for example, TTTCGCGCC (SEQ ID NO:2) (E2F binding site of the DHFR gene) or TTTCGCGGC (SEQ ID NO:3) (E2F-1 binding site of the E2F-1 gene).

In addition, the promoter module according to the invention (b) comprises a nucleotide sequence termed cell cycle genes homology region (CHR). This nucleotide sequence, which is likewise necessary for repression, cooperates with the E2F binding site during repression and is located downstream from the E2F site at the 3' end. Thus in one embodiment, this sequence comprises the nucleotide sequence TAGGAAA (SEQ ID NO:4) or a functionally similar (analogous) sequence which is able to cooperate with the E2F binding site in the cell cycle regulated expression.

Thus in one embodiment, in a nucleic acid construct according to the invention, the promoter module (b) inhibits the effect of the activator sequence (which is located upstream) during the G0 and G1 phases of the cell cycle. Thus, the expression of the gene (c), which is located downstream, is inhibited during G0 and G1.

In yet another embodiment, the promoter module (b) further comprises a transcription-initiating sequence.

Sequence 1 and Sequence 4 of the promoter module according to the invention are present in the following arrangement: CTTGGCGGGAGATAGGAAA (SEQ. ID NO:13). Thus in one embodiment, the promoter module comprises this sequence. In another embodiment, the promoter module of the invention comprises the sequence: CTTGGCGGGAGATAGGAAAGT (SEQ. ID NO:5).

The present invention also relates to isolated cells which comprise a nucleic acid construct according to the invention. Suitable cells include, but are not limited to, endothelial cells, lymphocytes, macrophages, glia cells or tumor cells.

C. Constructs for Therapeutic Use

The present invention relates to nucleic acid constructs which can be used in genetic engineering and, in particular, in the gene therapy of disorders.

In gene therapy, genes which are intended to be expressed in the body are introduced into the body. Regulation of the expression of these genes is important for the therapeutic effect of gene therapy. The present invention therefore relates to nucleic acid constructs which can be used in gene therapy. Techniques for gene therapy are well known to the skilled artisan. For example, WO 93/24640 and WO 95/11984, both of which are hereby incorporated by reference, disclose methods and compositions for in vivo gene therapy using nonviral or viral vector technology. In another example, WO 95/06743, hereby incorporated by reference, discloses a method whereby therapeutic nucleic acid constructs are introduced into a patient's isolated airway epithelial cells via transformation with a viral (AAV) vector containing a construct. The transformed cells are then administered to the patient. The technology for the various nonviral or viral vectors, that can be used as carriers for the constructs of this invention and applied to cells in vitro or injected or applied in vivo to patients are likewise well known to the skilled artisan.

In one embodiment, the nucleic acid construct is used for cell-specific, cell cycle-regulated expression of at least one structural gene. In another embodiment, the nucleic acid construct is used for virus-specific, cell cycle-regulated expression of at least one structural gene. In another embodiment, the nucleic acid construct is used for a metabolic specific, cell cycle-regulated expression of at least one structural gene.

A nucleic acid construct according to the invention, or the cell containing the latter, is used in the treatment of a disorder which is characterized by excessive cell proliferation, such treatment comprising introduction of a nucleic acid construct according to the invention into a target cell. By virtue of the structure of the construct, it is expressed during the stage of cell proliferation. Examples of disorders characterized by excess of cell proliferation, are tumor diseases, Leukemias, inflammatory reactions, autoimmune reactions, psoriasis and chronic viral infections. Such diseases can be treated by systemic or local application of the constructs of the invention. Expression of such constructs in the respective proliferative cell population will be controlled by the cell specific or virus specific activator sequence and the cell cycle specific promoter module. The expression product of the construct of the invention will directly or indirectly inhibit cell-proliferation or kill the proliferating cells.

For treatment of other disorders, the activator sequence and the structural gene for the active substance in the nucleic acid constructs according to the invention are selected depending on the purpose of use. In this regard, the invention comprises the following constructs and therapeutic methods.

1. Therapy of Tumors and Chronic Inflammations via Inhibition of Endothelial Cell Proliferation Tumors as well as chronic inflammations are characterised by the formation of new blood vessels by proliferating endothelial cells. In one embodiment, such proliferating endothelial cells are the target cells that are transformed by the constructs of the invention to express a protein that directly or indirectly inhibits the proliferation of endothelial cells and/or kills proliferating endothelial cells.

a. Activator sequences activated in endothelial cells

In one embodiment, activator sequences include those gene-regulatory sequences and elements from promoters for genes which code for proteins which are detectable in particular in endothelial cells. Some of these proteins have been described by Burrows et al. (Pharmac. Therp. 64, 155 (1994)) and Plate et al. (Brain Pathol. 4, 207 (1994)). These endothelial cell-specific proteins include in particular, for example, (a) brain-specific endothelial glucose 1 transporter The promoter sequence has been described by Murakami et al. (J. Biol. Chem. 267, 9300 (1992)).

(b) endoglin—The promoter sequence has been described by Bellon et al. (Eur. J. Immunol. 23, 2340 (1993)) and Ge et al. (Gene 138, 201 (1994)).

(c) VEGF receptors, of which two types have been identified (Plate et al., Int. J. Cancer 59, 520 (1994)): (1) VEGF receptor 1 (flt-1) (de Vries et al., Science 255, 989 (1992)) and (2) VEGF receptor 2 (flk-1, KDR) (Terman et al., BBRC 187, 1579 (1992)). Both receptors are to be found almost exclusively on endothelial cells (Senger et al., Cancer Metast. Rev. 12, 303 (1993)).

(d) Other endothelium-specific receptor tyrosine kinases, such as til-1 or til-2 (Partanen et al., Mol. Cell. Biol. 12, 1698 (1992), Schnürch and Risau, Development 119, 957 (1993), Dumont et al., Oncogene 7, 1471 (1992)); the B61 receptor (Eck receptor) (Bartley et al., Nature 368, 558 (1994), Pandey et al., Science 268, 567 (1995), van der Geer et al., Ann. Rev. Cell. Biol. 10, 251 (1994)).

(e) B61—The B61 molecule is the ligand for the B61 receptor. (Holzman et al., J. Am. Soc. Nephrol. 4, 466 (1993), Bartley et al., Nature 368, 558 (1994)).

(f) Endothelin such as endothelin B. The promoter sequence has been described by Benatti et al., J. Clin. Invest. 91, 1149 (1993); endothelin-1—The promoter sequence has been described by Wilson et al., Mol. Cell. Biol. 10, 4654 (1990).

(g) Endothelin receptors, in particular the endothelin-B receptor (Webb et al., Mol. Pharmacol. 47, 730 (1995), Haendler et al., J. Cardiovasc. Pharm. 20, 1 (1992)).

(h) Mannose 6-phosphate receptors—The promoter sequences have been described by Ludwig et al. (Gene 142, 311 (1994)), Oshima et al. (J. Biol. Chem. 263, 2553 (1988)) and Pohlmann et al. (PNAS USA 84, 5575 (1987)).

(i) von Willebrand factor—The promoter sequence has been described by Jahroudi and Lynch (Mol. Cell. Biol. 14, 999 (1994)), Ferreira et al., Biochem. J. 293, 641 (1993) and Aird et al., PNAS USA 92, 4567 (1995)).

(j) IL-1α, IL-1β—The promoter sequences have been described by Hangen et al., Mol. Carcinog. 2, 68 (1986), Turner et al., J. Immunol. 143, 3556 (1989), Fenton et al., J. Immunol. 138, 3972 (1987), Bensi et al., Cell Growth Diff. 1, 491 (1990), Hiscott et al., Mol. Cell. Biol. 13, 6231 (1993) and Mori et al., Blood 84, 1688 (1994).

(k) IL-1 receptor—The promoter sequence has been described by Ye et al., PNAS USA 90, 2295 (1993). (1) Vascular cell adhesion molecule (VCAM-1)—The promoter sequence of VCAM-1 has been described by Neish et al., Mol. Cell. Biol. 15, 2558 (1995), Ahmad et al., J. Biol. Chem. 270, 8976 (1995), Neish et al., J. Exp. Med. 176, 1583 (1992), Iademarco et al., J. Biol. Chem. 267, 16323 (1992) and Cybulsky et al., PNAS USA 88, 7859 (1991).

In addition to the above-described activator sequences, synthetic activator sequence may be used as alternatives to natural endothelium-specific promoters. Such synthetic activator sequences may comprise oligomerized natural binding sites for transcription factors which are preferentially or selectively active in endothelial cells. One example thereof is the transcription factor GATA-2 whose binding site in the endothelin-1 gene is 5'-TTATCT-3' (Lee et al., Biol. Chem. 266, 16188 (1991), Dorfmann et al., J. Biol. Chem. 267, 1279 (1992) and Wilson et al., Mol. Cell. Biol. 10, 4854 (1990)).

b. Activator sequences activated in cells adjacent to activated endothelial cells When endothelial cells are proliferating, adjacent cells become accessible to macromolecules from the blood due to "tight junctions". These functional and anatomic interrelations mean that cells in the vicinity of activated endothelial cells are target cells for the purpose of this invention. The following activator sequences, present in adjacent cells, are suitable for preparing constructs according to the invention.

(a) VEGF—The gene-regulatory sequences for the VEGF gene are (i) the promoter sequence of the VEGF gene (5' flanking region) (Michenko et al., Cell. Mol. Biol. Res. 40, 35 (1994), Tischer et al., J. Biol. Chem. 266, 11947 (1991)); (ii) the enhancer sequence of the VEGF gene (3' flanking region; (Michenko et al., Cell. Mol. Biol. Res. 40, 35 (1994)); (iii) the c-Src gene (Mukhopadhyay et al., Nature 375, 577 (1995), Bonham et al., Oncogene 8, 1973 (1993), Parker et al., Mol. Cell. Biol. 5, 831 (1985), Anderson et al., Mol. Cell. Biol. 5, 1122 (1985)); and (iv) the V-Src gene (Mukhodpadhyay et al., Nature 375, 577 (1995), Anderson et al., Mol. Cell. Biol. 5, 1122 (1985), Gibbs et al., J. Virol. 53, 19 (1985))

(b) Steroid hormone receptors and their promoter elements (Truss and Beato, Endocr. Rev. 14, 459 (1993)), such as the mouse mammary tumor virus promoter—The cDNA sequence of the promoter region of the long terminal repeat region of MMTV has been described by Chalepakis et al., Cell 53, 371 (1988) and Truss and Beato (Endocr. Rev. 14, 459 (1993)).

c. Structural genes for antitumor (or antiinflammatory) activity substances

An "antiiflammatory" substance, as used in this application, may have one or more of the following characteristics: inhibition of endothelial cell proliferation, inhibition of angiogenesis, cytostatic or cytotoxic properties, or the ability to convert a prodrug into an active drug with antitumoral or antiinflammatory properties. As used in this application, an "antitumor" substance may have one or more of the preceding properties. In addition, an "antitumor" substance according to the invention may be a substance that induces inflammation. These substances are described in more detail below.

i) Proliferation inhibitors

An "antiinflammatory" substance for the purpose of this invention includes a protein which inhibits the proliferation of endothelial cells ("cell cycle inhibitor" or "proliferation inhibitor"). In addition, the skilled artisan will recognize that an "antitumor" substance may also have the property of inhibition of proliferation. DNA sequences encoding such proteins are used in making DNA constructs according to the invention. Proteins that inhibit proliferation include, for example:

(a) the retinoblastom protein (pRb/p110) or its analogues p107 and p130 (La Thangue, Curr. Opin. Cell Biol. 6, 443 (1994))

(b) the p53 protein (Prives et al., Genes Dev. 7, 529 (1993))

(c) the p21 (WAF-1) protein (El-Deiry et al., Cell 75, 817 (1993))

(d) the p16 protein (Serrano et al., Nature 366, 704 (1993), Kamb et al., Science 264, 436 (1994), Nobori et al., Nature 368, 753 (1994))

(e) other cdk inhibitors (reviewed by Pines, TIBS 19, 143 (1995))

(f) the GADD45 protein (Papathanasiou et al., Mol. Cell Biol. 11, 1009 (1991), Smith et al., Science 266, 1376 (1994))

(g) the bak protein (Farrow et al., Nature 374, 731 (1995), Chittenden et al., Nature 374, 733 (1995), Kiefer et al., Nature 374, 736 (1995))

In order to prevent rapid intracellular inactivation of these cell cycle inhibitors, the genes which are used in a preferred embodiment are those which have mutations in portions of the gene encoding an "inactivation site" of the expressed protein without these impairing their function thereby. Thus, for example, the retinoblastoma protein (pRb) and the related p107 and p130 proteins are inactivated by phosphorylation. Thus, a pRb/p110, p107 or p130 cDNA sequence which is preferably used has a point mutation in such a way that the phosphorylation sites of the encoded protein are replaced by amino acids which cannot be phosphorylated. Examples of that exchange of amino acids of the retinoblastoma protein (pRb/p110) are described by Hamel et al., Mol. Cell Biol. 12, 3431 (1992)). One example is the exchange of amino acids Thr-256, Ser-601, Ser-605, Ser-780, Ser-786, Ser-787 and Ser-800 with Ala, and exchange of amino acid Thr-350 with Arg and replacement of amino acid Ser-804 with Glu. Similar changes are made in the DNA sequences encoding the p107 or p130 proteins.

i-a) Therapeutic use

A construct described in this section is administered to a patient in need of treatment for a tumor, an inflammatory disorder or a disorder characterized by excess endothelial cell proliferation. By using a construct that is expressed in endothelial cells or in cells adjacent to endothelial cells only during proliferation, the expression of the structural gene is restricted to those cells. The expression inhibits proliferation of or kills endothelial cells at the site of the expression and by that destroys angiogenesis and inhibits blood flow which results in inhibition of tumor growth or in reduction of inflammation.

ii) Angiogenesis inhibitors

An "antiinflammatory" or "antitumor" substance, as used in this application, furthermore includes a protein which induces thrombosis or inhibits angiogenesis. DNA sequences encoding such proteins are used in making DNA constructs according to the invention. These proteins include, for example:

(a) tissue factor (TF) and procoagulant fragments thereof (Morrissey at al., Cell 50, 129 (1987), Scarpati et al., Biochem. 26, 5234 (1987), Spicer et al., PNAS USA 84, 5148 (1987), Rehemtulla et al., Thromb. Heamost. 65, 521 (1991))

(b) plasminogen activator inhibitor 1 (PAI-1)

(c) PAI-2

(d) PAI-3

(e) angiostatin (f) interferons
(g) IFNα
(h) IFNβ
(i) IFN-gamma
(j) platelet factor 4
(k) IL-12
(l) TIMP-1
(m) TIMP-2
(n) TIMP-3
(o) leukemia inhibitory factor (LIF)

The genes encoding these proteines are described in PCT/EP95/03370, hereby incorporated by reference.

ii-a) Therapeutic use

Therapeutic methods are described in section (1) (c) (i-a) above.

iii) Cytostatic and cyto toxic proteins

In yet another embodiment, an antitumor or antiinflammatory substance also includes a protein which has, directly or indirectly, a cytostatic effect on tumors. DNA sequences encoding such proteins are used in making DNA constructs according to the invention. These proteins include:

(a) antibodies and antibody cleavage products specific for proliferating endothelial cells or for tumor cells.
(b) perforin
(c) granzyme
(d) IL-2
(e) IL-4
(f) IL-12
(g) interferons such as, for example, IFN-α, IFN-β, IFN-gamma
(h) Tumor necrosis factors (TNF), such as TNF-α and TNF-β
(i) oncostatin M References for genes coding for these proteins are cited in PCT/EP95/03370.
(j) magainin and magainin derivatives (Cruciani et al. PNAS 88, 3792 (1991); Peck-Miller et al.; Cancer Chemoth. Pharmac. 32, 109, (1993))
(k) sphingomyelinase (Jarvis et al. PNAS-USA 91, 73 (1994))

iii-a) Therapeutic use

Therapeutic methods are described in section (1) (c) (i-a) above.

iv. Inflammation inducers

In yet another embodiment, an antitumor substance furthermore includes a protein which, where appropriate, further stimulates antitumor inflammations via leukocycte or complement activation and thus contributes to the elimination of tumor cells. DNA sequences encoding such proteins are used in making DNA constructs according to the invention. These proteins include, in particular, for example:

(a) RANTES (MCP-2)
(b) monocyte chemotactic and activating factor (MCAF)
(c) macrophage inflammatory protein-1 (MIP-1a, -β)
(d) neutrophil activating protein-2 (NAP-2)
(e) interleukins, such as IL-3, IL-5 and IL-7, IL-8, IL-11, and IL-13
(f) human leukemia inhibitory factor (LIF)
(g) GM-CSF
(h) G-CSF
(i) M-CSF References for genes coding for these proteins are cited in PCT/EP95/03370.
(j) bacterial proteins which activate complement, such as porins of Salmonella typhi murium (Galdiero et al., Infection and Immunity 46, 559 (1984)), "clumping" factors of Staphylococcus aureus (Espersen Acta Path. Microb. et Imm. Scandin. Sect. C 93, 59 (1985)), modulins of gram-negative bacteria (Henderson et al., Infam. Res. 44, 187 (1995)), "Major outer membrane protein" of legionella (Bellinger-Kawahara et al., J. Exp. Med. 172, 1201 (1990) or of Haemophilus influenza Typ B (Hetherington et al., Infection and Immunity 60, 19 (1992)) or of Klebsiella (Alberti et al., Infection and Immunity 61, 852 (1993)) or M-molecules of streptococci group G (Campo et al., J. Infect. Dis. 171, 601 (1995)).
(k) cobra venom factor (CVF) and sequences thereof, that functionally correspond to human complement factor C3b, that means which bind to complement factor B and form, after cleavage by factor D, a convertase cleaving the complement factor C3. The DNA sequence for CVF were published by Fritzinger et al., Proc. Natl. Acad. Sci. USA 91, 12775 (1994)

the human complement factor C3 or its fragment C3b. The DNA sequence for C3 and its fragments was published by De Bruijn et al., Proc. Natl. Acad. Sci. USA 82, 708 (1985)

fragments of the human complement factor C3, that are similar to CVF. Such fragments were published by O'Keefe et al., J. Biol. Chem. 263, 12690 (1988).

(l) It is also possible to use as active substance for the purpose of the invention fusion proteins comprising one of the listed cytokines and the Fc part of human immunoglobulin. DNA sequences encoding fusion proteins of this type and their preparation have been described in EP 0464 633 A1, which is hereby incorporated by reference. Such fusion proteins have an increased blood half life time that results in a prolonged activity.

iv-a) Therapeutic use

Constructs according to this invention are injected into the tumor of the patients or systemically to transduce proliferating endothelial cells or proliferating cells in their neighbourhood to express the inflammatory protein. The resulting inflammation contributes to eliminate the tumor tissue.

v. Enzymes for activating precursors of cytostatics

In yet another embodiment, an antitumor or antiinflammatory substance, as used in this application, also includes an enzyme which is able to convert a precursor of an antitumor active substance into an antitumor active substance. DNA sequences encoding such proteins are used in making DNA constructs according to the invention.

Enzymes of this type which cleave inactive precursor substances (prodrugs) to give active cytostatics (drugs), and the relevant prodrugs and drugs in each case have been described by Deonarain et al. (Br. J. Cancer 70, 786 (1994), von Mullen, Pharmac. Ther. 63, 199 (1994)) and Harris et al., Gene Ther. 1, 170 (1994), each of which is hereby incorporated by reference. See also Hay et al., Drugs of the Future 21, 917 (1996) and Sedlack et al. Contributions to Oncology No. 43, Karger 1992.

For example, the DNA sequence of one of the following enzymes may be used:

(a) herpes simplex virus thymidine kinase, (Garapin et al., PNAS USA 76, 3755 (1979), Vile et al., Cancer Res. 53, 3860 (1993), Wagner et al., PNAS USA 78, 1441 (1981), Moelten et al., Cancer Res. 46, 5276 (1986), J. Natl. Cancer Inst. 82, 297 (1990))
(b) varicella zoster virus thymidine kinase, (Huber et al., PNAS USA 88, 8039 (1991), Snoeck, Int. J. Antimicrob. Agents 4, 211 (1994))

(c) bacterial nitro reductase, (Michael et al., FEMS Microbiol. Letters 124, 195 (1994), Bryant et al., J. Biol. Chem. 266, 4126 (1991), Watanabe et al., Nucleic Acids Res. 18, 1059 (1990))

(d) bacterial β-glucuronidase, (Jefferson et al., PNAS USA 83, 8447 (1986))

(e) plant β-glucuronidase from Secale cereale, (Schulz et al., Phytochemistry 26, 933 (1987))

(f) human β-glucuronidase,(Bosslet et al., Br. J. Cancer 65, 234 (1992), Oshima et al., PNAS USA 84, 685 (1987))

(g) human carboxypeptidase (CB), for example, mast cell CB-A (Reynolds et al., J. Clin. Invest. 89, 273 (1992)), pancreatic CB-B (Yamamoto et al., J. Biol. Chem. 267, 2575 (1992), Catasus et al., J. Biol. Chem. 270, 6651 (1995)), bacterial carboxypeptidase (Hamilton et al., J. Bacteriol. 174, 1626 (1992), Osterman et al., J. Protein Chem. 11, 561 (1992)), bacterial β-lactamase (Rodrigues et al., Cancer Res. 55, 63 (1995), Hussain et al., J. Bacteriol. 164, 223 (1985), Coque et al., Embo J. 12, 631 (1993)), bacterial cytosine deaminase (Mullen et al., PNAS USA 89, 33 (1992), Austin et al., Mol. Pharmac. 43, 380 (1993), Danielson et al., Mol. Microbiol. 6, 1335 (1992)), human catalase or peroxidase (Ezurum et al., Nucl. Acids Res. 21, 1607 (1993)), (h) phosphatase, such as human alkaline phosphatase (Gum et al., Cancer Res. 50, 1085 (1990)), human prostatic acid phosphatase (Sharieff et al., Am. J. Hum. Gen. 49, 412 (1991), Song et al., Gene 129, 291 (1993), Tailor et al., Nucl. Acids Res. 18, 4928 (1990)), type 5 acid phosphatase (Gene 130, 201 (1993))

(i) oxidase, such as human lysyl oxidase (Kimi et al., J. Biol. Chem. 270, 7176 (1995)), human acidic D-aminoxidase (Fukui et al., J. Biol. Chem. 267, 18631 (1992))

(j) peroxidase, such as human glutathione peroxidase (Chada et al., Genomcis 6, 268 (1990), Ishida et al., Nucl. Acids Res. 15, 10051 (1987)), human eosinophil peroxidase (Ten et al., J. Exp. Med. 169, 1757 (1989), Sahamaki et al., J. Biol. Chem. 264, 16828 (1989)), human thyroid peroxidase (Kimura, PNAS USA 84, 5555 (1987)).

To facilitate secretion of such enzymes the homologous signal sequence present in the DNA sequence is replaced in each case by a heterologous signal sequence which improves extracellular release. Thus, for example, the signal sequence of β-glucuronidase (DNA position 27 to 93; Oshima et al., PNAS 84, 685 (1987)) can be replaced by the signal sequence for immunoglobulin (DNA position<63 to>107; Riechmann et al., Nature 332, 323 (1988)).

In another embodiment, DNA sequences encoding an enzyme as described above contain point mutations that result in decreased storage of the enzyme in lysosomes and increased storage of enzyme. For example, such mutations of β-Glucuronidase were published by Shiplex et al. J. Biol. Chem. 268, 12193, (1993).

v-a) Therapeutic use

Constructs according to this method are injected systemically into the patient or into tumor of the patient to transduce proliferating endothelial cells or proliferating cells in their neighbourhood to express the enzyme coded by the structural gene. Subsequently, the prodrug is injected systemically and converted by the expressed enzyme into the cytotoxic drug, that kills or inhibits proliferating endothelial cells such as tumor cells in tumor diseases. Neighbouring proliferating cells are also killed.

c. Combination of a plurality of antitumor or antiinflammatory substances

The invention furthermore relates to nucleic acid constructs comprising DNA sequences a plurality of identical antitumor or antiinflammatory substances ("A,A") or of different antitumor substances ("A,B"). For expression of two DNA sequences, the cDNA of an internal ribosome entry site (IRES) may be interpolated as regulatory element.

| Activator sequence | Cell cycle-regulated promoter module | Antitumor substance A | Internal ribosome entry site | Antitumor substance A or B |
|---|---|---|---|---|

IRESs of this type have been described, for example, by Mountford and Smith, TIG 11, 179 (1995), Kaufman et al., Nucl. Acids Res. 19, 4485 (1991), Morgan et al., Nucl. Acids Res. 20, 1293 (1992, Dirks et al., Gene 128, 247 (1993), Pelletier and Sonenberg, Nature 334, 320 (1988) and Sugitomo et al., BioTechn. 12, 694 (1994).

Thus, the cDNA of the IRES sequence of poliovirus (position 140 to 630 of the 5' UTR; Pelletier and Sonenberg, Nature 334, 320 (1988)) can be used to link the DNA of the antiinflammatory substance A (at the 3' end) and the DNA of the antiinflammatory substance B (at the 5' terminus).

An active substance of this type has, depending on the combination, an additive (A+A, A+B1) or synergistic effect for the purpose of the invention.

2. Active Substance for Remedying Deficient Production of Blood Cells a. Selection of the activator sequence for hemopoietic cells The activator sequence used for the purpose of the present invention is a gene-regulatory sequence or an element of a gene which encodes a protein which is expressed strongly or selectively in hemopoietic cells. Gene-regulatory sequences of this type include promoter sequences for genes of a cytokine or its receptor, the expression of which in immature hemopoietic cells (or in adjacent cells such as, for example, the stroma), precedes the subsequent cytokine which acts on the hemopoietic cells and is required as active substance. Cytokines of this type which act on immature hemopoietic cells are, for example, such as stem cell factor, IL-1, IL-3, IL-6, GM-CSF or Thrombocytopoietin. References for such cythokines are given in PCT/EP95/03371, which is hereby incorporated by reference.

In another embodiment the activator sequence is metabolic specific. Examples of metabolic (hypoxia) activatable activator sequences are described by Semenza et al. PNAS 88, 5680 (1991) or McBurney et al. Nucl. Acids Res. 19, 5755 (1991), hereby incorporated by reference.

b. Selection of the structural genes for active substances for hemopoietic cells An "active substance for hemopoietic cells," as used in this application, means protein that effects proliferation and/or differentiation of blood cells. Examples of such a substances are listed in PCT/EP95/03371, hereby incorporated by reference.

c. Therapeutic use

Constructs according to this method are injected into patients suffering from an anemia, leukopenia or thrombocytopenia to transduce their stem cells to express the respective cytokines. As a result of this expression, erythropoieses, leukozythopoieses and/or thrombocytopoiesis is stimulated.

3. Active Substance for the Therapy of Autoimmune Diseases, Allergies, Inflammations and to Prevent Organ Rejections a. Selection of the activator sequence The activator sequences to be used are (1) the promoter sequences from genes strongly activated in macrophages or lymphocytes or (2) are from genes for proteins which are produced at high levels during the immune response in macrophages and/or in lymphocytes. Examples of such proteins are (a) IL-1
(b) IL-1-β
(c) IL-1 receptor
(d) IL-2
(e) IL-2 receptor
(f) IL-3
(g) IL-3 receptor
(h) IFN-gamma
(i) IL-4
(j) IL-4 receptor
(k) IL-5
(l) IL-6
(m) LIF
(n) IL-7
(o) IL-10
(p) IL-11
(q) IL-12
(r) IL-13
(s) GM-CSF
(t) GM-CSF receptor
(u) integrin beta 2 proteins Nucleotide sequences for this proteins are known in the art and are given in PCT/EP95/03371, hereby incorporated by reference.

b. Selection of the genes for active substances for the therapy of autoimmune diseases, allergies, inflammations and to prevent organ rejections A gene encoding an active substance for the purpose of the invention is the DNA sequence for a cytokine, a chemokine, a growth factor or one of their inhibitors, an antibody, an antibody fragment, an enzyme inhibitor or an enzyme. The choice of the active substance depends on the basic disorder to be treated and the promoter sequence selected. Examples for the selection of activator sequences and structural genes appropriate for treatment of the autoimmune diseases, allergy, inflammation or for prevention of organ rejection are given in PCT/EP95/03371. which is hereby incorporated by reference.

c. Therapeutic Methods

Constructs according to this invention are injected into patients suffering from autoimmune disease, allergies, inflammations or organ rejections to transform their lymphocytes or macrophages to express the selected structural gene. The expressed protein directly or indirectly inhibits the function or proliferation of the lymphocytes or macrohages or of a subset of these cells. As a result of that inhibition, the autoimmune disease, the allergy, the inflammation or the organ rejection is reduced.

4. Active Substance for the Treatment of Arthritis a. Selection of the activator sequence for arthritis The activator sequence means a nucleotide sequence (promoter or enhancer sequence) with which transcription factors are formed or actively interact in synovial cells and inflammatory cells. For the purpose of this invention, the preferred promoter sequences include gene-regulatory sequences and elements from genes which code for proteins which are particularly expressed in synovial cells and inflammatory cells. Examples for such proteins are outlined in PCT/EP95/03371, which is hereby incorporated by reference.

b. Selection of the structural genes for active substances for arthritis

The active substance for the purpose of the invention means a DNA sequence whose expressed protein directly or indirectly inhibits the inflammation, for example in the joint, and/or promotes reconstitution of extracellular matrix (cartilage, connective tissue) in the joint. Examples of such substances are given in PCT/EP95/03371.

c. Therapeutic use

The constructs according to this invention are injected into the diseased joint to transduce synovial cells and/or macrophages to express the structural gene expressing the therapeutic protein.

5. Antiinfective Substance

The active substance can be prepared in two forms: (1) for the therapy of viral infections and invasions by parasites or (2) for the prophylaxis of infectious diseases due to viruses, bacteria or parasites.

Vaccines are used for the prophylaxis of infectious diseases. However, the possibilities for preparing effective vaccines by conventional means are limited (Brown, Int.J. Technol. Assessm. Health Care 10, 161 (1994), Ellis, Adv. Exp. Med. Biol. 327, 263 (1992), Arnon et al., FASEB J. 6, 3265 (1992)). Thus, the technology of DNA vaccines has been developed. However, these DNA vaccines give rise to questions about safety and side effects (Fynan et al., Int. J. Immunopharm. 17, 79 (1995), Donnelly et al., Immunol. 2, 20 (1994)).

Active substances for the prophylaxis of infectious diseases for the purpose of this invention are distinguishable from prior art substances because of their cell specificity and cell cycle regulation. These characteristics result in a high degree of safety of these substances.

a. Selection of the activator sequence i) For the therapy of infectious diseases The activator sequence to be chosen comprises promoter sequences from cellular genes whose activity is altered in particular by infections with bacteria or parasites, or the promoter sequences to be chosen are those from viruses which transform the cells infected by them and stimulate proliferation. These viruses include, for example, HBV, HCV, HSV, HPV, HIV, EBV and HTLV.

ii) For the prophylaxis of infectious diseases

The activator sequence comprises promoter sequences that are strongly activated in endothelial cells, muscle cells, lymphocytes or macrophages or that belong to cellular genes coding for proteins that are highly expressed in endothelial cells, muscle cells, macrophages or lymphocytes.

b. Selection of the structural genes for active substances i. For the therapy of infectious diseases The active substance to be selected is the DNA of a protein which has cytostatic, cytotoxic, antibacterial or antiviral effects. Examples of cytotoxic or cytostatic proteins are listed above. Antibodies or antibody fragments are exemplary antibacterial or antiviral proteins. As noted above, for some substances, enzymatic conversion of a precursor to the active form is required. If such conversion is required, the antibacterial, antiviral, cytotoxic, or antiparasitic substance is added after an enzyme-encoding construct according to the invention has already been administered.

Active substances for antiviral proteins for the purpose of this invention are furthermore cytokines and growth factors with antiviral activity. These include, for example, DNA sequences encoding the following active substances: IFN-α, IFN-β, IFN-gamma, TNF-β, TNF-α, IL-1 and TGF-β. However, the following DNA sequences, which encode fusion proteins comprising the following peptides, may also be used: (1) a cytokine, growth factor or the extracellular part of an aforementioned receptor for a molecule of this type and (2) the Fc part of human immunoglobulin. DNA sequences of this type and their preparation have been described, for example, in EP 0464 633 A1, which is hereby incorporated by reference.

ii. For the prophylaxis of infectious diseases

In one embodiment, the active substance is an antibody or of an antibody fragment specific for the pathogen. In another embodiment, the active substance is a protein which is formed by the pathogen which leads, through an immune response, i.e. by antibody binding and/or by cytotoxic T lymphocytes, to neutralization and/or killing of the pathogen. Neutralizing antigens of this type are known as immunizing antigens (see review by Ellis, Adv. Exp. Med. Biol. 327, 263 (1992)). DNA sequences encoding such proteins are used to make constructs according to the invention.

c. Therapeutic Methods

Constructs according to this invention are applied orally, or injected locally or systemically, to transduce infected cells or endothelial cells, muscle cells, macrophages or lymphocytes to express the therapeutic protein or the immunogen.

6. Active Substance for the Treatment of Leukemias and Tumors a. Selection of the activator sequence for leukemias and tumors The activator sequence provided is a nucleotide sequence (promoter or enhancer sequence) with which transcription factors which are formed or active in leukemia cells or tumor cells interact. However, for the purpose of this invention, activator sequences include gene-regulatory sequences and elements of genes which encode proteins formed in particular in tumor cells or leukemia cells. Examples are cited in PCT/EP95/03371.

b. Selection of the structural genes for active substances for leukemias and tumor cells The active substance for the purpose of the invention means a protein that inhibits the proliferation of cells, in particular also of tumor cells or leukemia cells. These cell cycle inhibitors include, for example, the DNA sequences for inhibitory cytostatic and cytotoxic proteins and enzymes that have already been described. A cell cycle inhibitor furthermore means a DNA sequence which expresses a protein which has, directly or indirectly, a cytostatic or cytotoxic effect on leukemias or tumors. Such proteins have already been described in the preceding chapters. DNA sequences encoding such proteins are used to make constructs according to the invention.

c. Therapeutic Methods

Suitable therapeutic methodology is described in section 5(b) above.

7. Active Substance for Inhibiting the Proliferation of Smooth Muscle Cells in Vascular Occlusions a. Selection of the activator sequence for smooth muscle cells In one embodiment, the activator sequences are gene-regulatory sequences or elements of genes which encode proteins which are particularly formed in smooth muscle cells. Examples are described in section 1b and in PCT/EP95/03368.

b. Selection of the structural genes for active substances for smooth muscle cells An active substance for the purpose of the invention means protein that inhibits the proliferation of smooth muscle cells. These inhibitors of proliferation include the proteins mentioned above in sections (1) (c) (i), (iii) and (iv). However, the active substance is also an enzyme which converts an inactive precursor of a cytostatic into a cytostatic, such as those substances listed above. DNA sequences encoding such proteins are used to make constructs according to the invention.

c. Therapeutic use

The constructs according to this invention are injected into the bloodstream to transform smooth muscle cells so that they express the anti-proliferative or cytotoxic protein or express the enzyme for conversion of a subsequently injected prodrug into a cytostatic drug.

8. Active Substance for Inhibiting or Activating Coagulation or Modulating the Cardiovascular System a. Selection of the activator sequence for inhibiting or activating coagulation The activator sequences to be used for the purpose of the invention may be gene-regulatory sequences or elements of genes which encode proteins which are detectable in smooth muscle cells, in activated endothelial cells, in activated macrophages or in activated lymphocytes.

i) Smooth muscle cells

Examples of promoter sequences for genes in smooth muscle cells are described in section (1) (b) and in PCT/EP95/03368.

ii) Activated endothelial cells or cells adjacent to activated endothelial cells Examples of proteins which are formed particularly in activated endothelial cells have been described by Burrows et al. (Pharmac. Therp. 64, 155 (1994)). These proteins which occur extensively in endothelial cells include, in particular, those proteins listed above (sections (1) (a) and (1) (b)) together with the promoter sequences of their genes.

iii) Activated macrophages and/or activated lymphocytes

An activator sequence for the purposes of this invention additionally means a promoter sequence from a gene encoding a protein which is formed extensively during the immune response in macrophages and/or in lymphocytes. Examples are listed in section (3) (a).

b. Selection of the structural genes for active substances for inhibiting or activating coagulation In one embodiment, the active substance for the purpose of this invention is a protein which inhibits, directly or indirectly, platelet aggregation or a coagulation factor, or stimulates fibrinolysis. Thus, an active substance of this type is referred to as an anticoagulant. The anticoagulants to be employed are genes for, for example, plasminogen activators (PA), for example tissue PA (tPA) or urokinase-like PA (uPA) or protein C, antithrombin III, C-1S inhibitor, α1 antitrypsin, the tissue factor pathway inhibitor (TFPI) or hirudin. References describing the genes for these proteins are listed as follows:

Tissue Plasminogen Activator (tPA) (Sasaki et al., Nucl. Acids Res. 16, 5695 (1988); Pennica et al., Nature 301, 214 (1983); Wei et al., DNA 4, 76 (1985); Harris et al., Mol. Biol. Med. 3, 279 (1986))

Urokinase-type Plasminogen Activator (uPA) (Miyake t al., J. Biochem. 104, 643 (1988); Nelles et al., J. Biol. Chem. 262, 5682 (1987))

Hybrids of tPA and uPA (Kalyan et al., Gene 68, 205 (1988); Devires et al., Biochem. 27, 2565 (1988))

Protein C (Foster et al., PNAS 82, 4573 (1985))

Hirudin (Maerki et al., Semin. Thromb. Hemostas. 17, 88 (1991); De Taxis du Poet al., Blood Coag. Fibrin. 2, 113 (1991); Harvey et al., PNAS USA 83, 1084 (1986); Sachhieri et al., EP 0324 712 BE1, EP 0142 860 B1))

Serin Proteinase Inhibitors (Serpine), as

C-1S-Inhibitor (Bock et al., Biochem. 25, 4292 (1986); Davis et al., PNAS USA 83, 3161 (1986); Que, BBRC 137, 620 (1986); Rauth et al., Proteine Sequences and Data Analysis 1, 251 (1988); Carter et al., Eur. J. Biochem. 173, 163 (19889; Tosi et al., Gene 42, 265 (1986); Carter et al., Eur. J. Biochem. 197, 301/1991); Eldering et al., J. Biol. Chem. 267, 7013 (1993))

α1-Antitrypsin (Tosi et al., Gene 42, 265 (1986); Graham et al., Hum Genetics 85, 381 (1990); Hafeez et al., J. Clin. Invest. 89, 1214 (1992); Tikunova et al., Bioorganicheskaja Khimia 17, 1694 (1991); Kay et al., Human Gene Ther. 3, 641 (1992); Lemarchand et al., Molekulaiaruaia Biologica 27, 1014 (1993); Lambach et al., Human Mol. Gen. 2, 1001 (1993))

Antithrombin III (Stackhouse et al., J. Biol. Chem. 258, 703 (1983); Olds et al., Biochem. 32, 4216 (1993); Laue et al., Nucl. Acids Res. 22, 3556 (1994))

Tissue Factor Pathway Inhibitor (TFPI) (Enjyoji et al., Genomics 17, 423 (1993); Wun et al., J. Biol. Chem. 263, 6001 (1988); Girard et al., Thromb. Res. 55, 37 (1989))

In another embodiment, an active substance for the purpose of this invention is also a protein which promotes blood coagulation. Examples of such proteins are, for example, blood plasma proteins such as factor VIII or factor IX. DNA sequences encoding such proteins are used to make constructs according to the invention. References describing the genes for these proteins are listed as follows:

F VIII (Kaufman, Ann. Hematol. 63, 155 (1991); Dwark et al., PNAS USA 92, 1023 (1995); Hoeben et al., J. Biol. Chem. 265, 7318 (1990); Truett et al., DNA 4, 333 (1985); Lynch et al., Gene Ther. 4, 259 (1993), Tuddenham et al., Nucl. Acids Res. 22, 3511 (1994))

F IX (Dai et al., PNAS USA 89, 10892 (1992); Smith et al., Nature Genet. 5, 397 (1993); Armentano et al., PNAS USA 87, 6141 (1990); Yao et al., PNAS USA 88, 8101 (1991); Kurachi et al., Thrombosis+Haemostasis 73, 333 (1995))

von Willebrand factor (Kaufman et al., Mol. Cell Biol. 9, 1233 (1989); Tuddenham, Blood Rev. 3, 1 (1989))

F XIII (Bottenus et al., Biochem. 29, 11195 (1990); Grundmann et al., Nucl. Acids Res. 18, 2817 (1990); Nouaka et al., Genomics 15, 535 (1993); Ichinose et al., PNAS USA 85 5829 (1988); Thrombosis and Haemostatis 58, 500 (1987))

PAI-1 (see PCT/EP95.03370)

PAI-2 c. Therapeutic use

Constructs according to the invention are injected into the bloodstream to transduce the endothelial cells, or cells adjacent to endothelial cells or macrophages or lymphocytes to express the respective protein.

9. Active Substance for Protecting from CNS Damage a. Activator sequences for an active substance for protecting from CNS damage i) Activator sequences activated in endothelial cells In one embodiment, this type of activator includes the promoter sequences for genes of proteins specific to endothelial cells. Examples of those promoter sequences are listed in chapter 1a) as well as in PCT/EP95/03369.

ii. Activator sequences activated in glial cells

One preferred activator sequence is a nucleotide sequence (promoter or enhancer sequence) with which transcription factors, which are formed or active to a particular extent in glial cells, interact. Examples of those activator sequences are listed in PCT/EP95/03369.

b. Choice of the structural genes for neurospecific factors

A "neurospecific factor" for the purpose of the invention means a DNA sequence which codes for a neuronal growth factor. Examples of those activator sequences are listed in PCT/EP95/03369.

c. Therapeutic use

Constructs according to the invention are preferably applied or injected into damaged tissue, into the area of damaged nerves or into the spinal cord or into the brain to transform endothelial cells or glia cells so that they express the therapeutic protein. In another embodiment the active substance to be used for the purpose of this invention is also a protein that modulates the cardiovascular system by inducing angiogenesis or by lowering blood pressure.

Examples for genes coding for such proteins are— angiogenesis factors, e.g.,

VEGF (Takeshita et al., J. Clin. Invest. 93, 662 (199?), Keck et al., Science 246, 1309 (1989); Tischer et al., J. Biol. Chem. 266, 11947 (1991))

FGF (Hersh et al., Gene Ther. 2, 124 (1995))—peptides for lowering blood pressure, e.g., Kallikrein (Wang et al., J. Clin. Invest. 95, 1710 (1995))

endothelial cell "nitric oxide synthase" (Lamas et al., PNAS USA 89, 6348 (1992), van der Leyen et al., PNAS USA 92, 1137 (1995))

The present invention is explained in detail by means of the following examples, which illustrate, but do not limit the scope of, the invention.

EXAMPLE 1

Biochemical Investigations

The interaction between the nucleotide sequence CTTGCGGGAG of the B-myb promoter and the E2F complexes was investigated by the electrophoretic mobility shift assay (EMSA) and by methylation protection footprinting. The EMSA was carried out as described by Barberis et al., Cell 50, 347 (1987).

For this purpose, the following Glutathion-S-Transferase (GST) fusion proteins were expressed in *E. coli* and purified by affinity chromatography:

E2F1, amino acids 87–1398. Helin et al., Cell 70, 337 (1992) and Kaelin et al., Genes Dev. 8, 2665 (1994), each of which is hereby incorporated by reference.

E2F4, total protein. Beijersbergen et al., Genes Dev. 8, 2680 (1994) and Ginsberg et al., Genes Dev. 8, 2665 (1994), each of which is hereby incorporated by reference.

pRb, amino acids 300–928. Bernards et al., Proc. Natl. Acad. Sci. USA 86, 6474 (1989), hereby incorporated by reference.

p107, amino acids 744–2460. Ewen et al., Cell 66, 1155 (1991), hereby incorporated by reference.

The purified proteins (about 100 ng) were incubated with about 0.5 pmol of a $^{32}$P-labeled probe in 15 µl of a buffer which contained 50 mM tris/HCl pH 8.0, 50 mM NaCl, 10% v/v glycerol, 0.2 mM EDTA, 1 mM DTT and 67 µg of poly[dA/dT]/µl at 22° C. for 30 min. The probes were labeled by insertion at the 5' protruding ends of 4–7 bases. The samples were fractionated in 4%, non-denaturing polyacrylamide gel in 0.5×TBE at 4° C. and 10 V/cm. The gels were exposed to an X-ray-sensitive film and quantitatively analyzed using a Molecular Dynamics phosphor imager.

The following probes were used:

B-myb [Lam et al., EMBO J. 12, 2705 (1993)],
5'-G G C G C C G A C G C A CTTG GCGGGAGATAGGAAAGTGGTTCTGTG (SEQ. ID NO: 6) (the E2F binding site is underlined)

mutated B-myb:
5'-G G C G C C G A C G C A CTT GGCTGGAGATAGGAAAGT GGTTCTGTG (SEQ. ID NO: 7)

the E2a adenovirus promoter:
5'-gatcGACTAGT TTCGCGCCCTTTCTActag (SEQ. ID NO: 8) (the lower case letters represent irrelevant sequences used for the fill-in labeling reactions)

control probe:
5'-GATCCTCTCACCTGCTGCTAG. (SEQ. ID NO: 9)

The methylation protection footprinting was carried out as follows: The oligonucleotide sequence encoding B-myb was labeled at the end, purified and combined with the non-coding strand. The binding reaction was carried out as already described for EMSA. Two microliters of 2% dimethyl sulfate (DMS) were added and the methylation reaction was stopped 3 minutes later by adding 2 μl of 60 mM β-mercaptoethanol. The samples were fractionated in a 4% gel and transferred to ion exchange paper. The bands were cut out, washed in TE buffer and eluted at 65° C. with TE buffer containing 1.5 M NaCl. The eluted DNA was extracted with chloroform, precipitated and dissolved in water. Amounts with equal reactivity of the band which remained at the point of application (free sample) and of the band which had migrated (complex) were cleaved with 10% piperidine at 95° C. for 30 minutes. The DNA was precipitated and loaded onto a 15% denaturing acrylamide gel.

Figure 1:
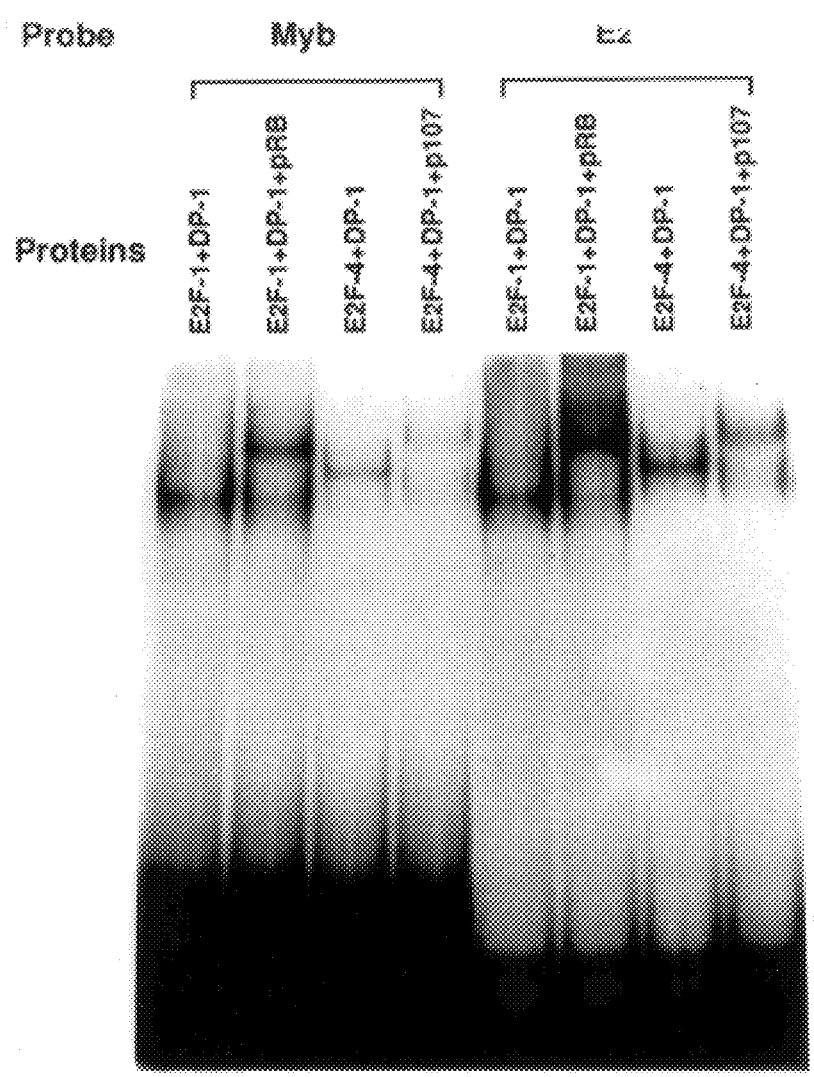
FIG. 1 shows interaction of the B-myb E2F binding site with various E2F-DP1 and E2F-DP1-p107 complexes. Complexes were prepared as recombinant GST fusion proteins and analyzed by EMSA (Barberis et al., Cell 50, 347 (1987)) with the aid of synthetic oligonucleotides which contained either the B-myb E2F binding site (Lam et al., EMBO J. 12, 2705 (1993)) or the E2F binding site of the E2a adenovirus promoter (Mudryj et al., EMBO J. 9, 2179 (1990)). The differences in the intensities seen between E2F1 and E2F4 complexes reflect the variations in the E2F protein preparations and do not reflect different binding affinities.

As shown in FIG. 1, E2F1-DP1, E2F1-DP1-pRb, E2F4-DP1 and E2F4-DP1-p107 bind to the E2F binding site of the B-myb promoter with comparable strength and with similar affinity as to the high-affinity E2a adenovirus promoter binding site (Mudryj et al., EMBO J. 9, 2179 (1990)). Quantification of the binding of the E2F complexes to the E2F binding site of the B-myb promoter was carried out on an EMSA gel with the aid of a phosphor imager which determined the amount of bound sample.

The following results were obtained (proportion of bound sample):

E2a promoter E2F binding site: 1.0% (E2F1-DP1) or 0.8% (E2F4-DP1)

B-myb: 0.7% (E2F1-DP1) or 2.0% (E2F1-DP1 or 2.0% (E2F4-DP1)

mutated B-myb:<0.01% negative control sample:<0.002%.

E2F4 complexes were selected for a dimethyl sulfate (DMS) protection footprinting analysis because the p107 protein is regarded as the essential binding protein in E2F complexes which react with the binding structure (Lam et al., EMBO J. 13, 871 (1994)). In addition, E2F4 in turn is the only known member of the E2F family which reacts with p107 (Beijersbergen et al., Genes Dev. 8, 2680 (1994) and Ginsberg et al., Genes Dev. 8, 2665 (1994)).

Figure 2:
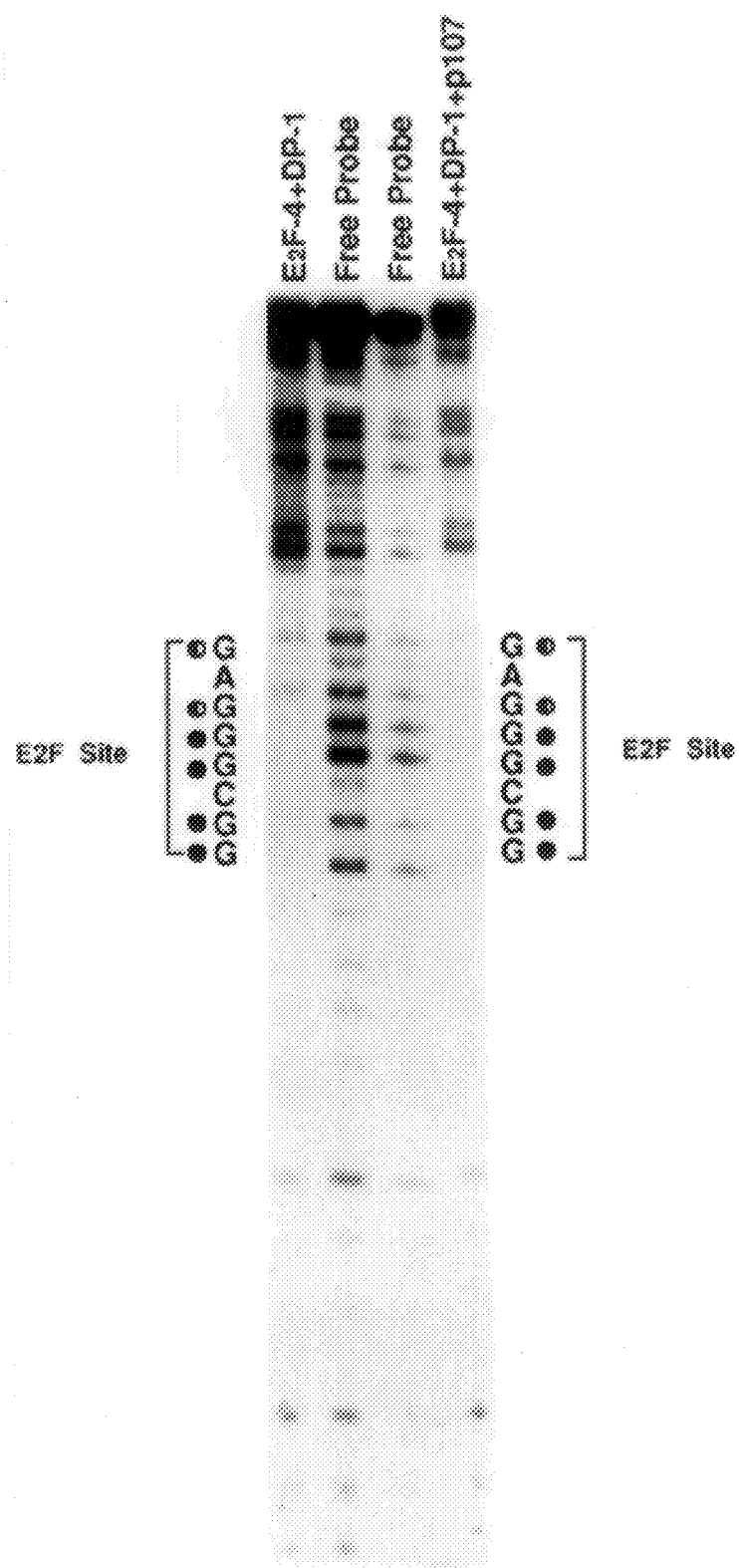
FIG. 2 shows methylation protection footprints of E2F2-DP1 and E2F4-DP1-p107 complexes. Methylated complexes were separated by an EMSA (see FIG. 1), and the protected guanines were analyzed (see text). Filled circles: complete protection; half-filled circles: partial protection.

As depicted in FIG. 2, the nucleotides were protected in the region of the E2F binding site (CTTGGC GGGAG, SEQ ID NO:20). Protected guanines are underlined, the two guanines located at the extreme 3' end being only partly protected downstream of the main E2F binding site. The results show furthermore that there were no detectable differences between the footprints obtained with E2F4-DP1 ("free E2F") and E2F4-DP1-p107. This observation shows clearly that E2F complexes bind to the DNA independently of the p107 protein and that this DNA binding can be detected by methylation protection footprinting. This is consistent with the finding that association and dissociation rates for E2F4-DP1 and E2F4-DP1-p107 complexes are very similar.

EXAMPLE 2

Investigations on Cells

In order to detect the binding of E2F to the B-myb promoter not only biochemically but also in living cells, NIH3T3 fibroblasts were synchronized in G0 by removal of serum and subsequently stimulated with 10% FCS. At various times after stimulation, in vivo investigations were carried out. The following parameters were investigated: cell cycle progression (by measuring DNA content), B-myb mRNA expression and binding of E2F complexes to the E2F binding site (protection from methylation).

As depicted in FIG. 3A, stimulation of quiescent cells by adding 10% FCS leads to onset of the S phase after about 12 hours. The onset of S phase was determined by a quantitative DNA analysis. Such a quantitative analysis is performed using a Flourescence Activating Cell Sorter, a techniques well known to the skilled artisan. Before onset of S phase, the cells contain a constant amount of DNA. From the onset until the end of S phase the DNA content of the cells increases. After completion of S phase the cell contain about twice as much DNA as before the onset of S phase due to chromosome duplication. Following S phase, cells divide and have the same DNA content as the starting amount.

As already shown by Lam et al., EMBO J. 12, 2705 (1993), B-myb mRNA expression increases 8 hours after stimulation (i.e. in the late G1 phase) and reaches the maximum after about 12 hours, i.e. at the time of onset of the S phase.
(FIG. 3B)

In order to analyze the role of the E2F binding site in the cell, genomic DMS footprinting was carried out as described by Lucibello et al., EMBO J. 14, 132 (1995) and by Pfeifer et al., Science 246, 810 (1989). The following primers were used for this purpose:

1. Primer: 5'-TCAGGACTCAGGCTGCT (Seq. ID 10)
2. Primer: 5'-CGAGCCGCTCCGGGCCCCAGG (Seq. ID 11)
3. Primer: 5'-GGCCCCAGGCGGTGCTCTCAGGCG. (Seq. ID 12)

Analysis of the G0 cells by genomic footprinting (FIG. 3C) showed a distinct occupation of the E2F binding site, both of the core element and of the two guanines located immediately downstream. Thus, the 6 guanines in positions −209, −208, −206, −205, −204 and −202 (relative to the ATG start codon (Lam et al., EMBO J. 12, 2705 (1993)) were unambiguously protected, although the last two showed only partial protection. This protection against methylation was similar to that in the purely biochemical investigation, which suggests that the protein complex providing intracellular protection is indeed E2F.

Similar results were obtained with all possible complexes containing E2F2, E2F3, E2F5, DP2 and DP3. As expected, no binding of E2F was found when a point mutation was inserted into the E2F binding site (CTTGGCGG→CTTGGCTG).

Analysis of serum-stimulated cells showed a similar protection of the E2F binding sequence after 4 hours. However, this protection was considerably reduced after 8 hours, and no significant protection was observable at later times. This decrease in protection took place at the same time as the increase in B-myb transcription. In contrast to the cell cycle-regulated protection of the E2F binding sequence from methylation, for example, the guanine in position −223, (position outside the E2F-binding site) showed unchanged hypermethylation throughout the cell cycle.

These results indicate that E2F complexes (which are indeed found on analysis of cell extracts in the late G1 and in the S phases, such as, for example, as free E2F and E2F complexes) are not bound to the B-myb E2F binding sequence in the living cell, i.e. in situ at the time of B-myb transcription.

These results furthermore prove that binding of E2F to the E2F binding sequence does not play a crucial part in the activation of transcription of the B-myb gene because this binding sequence is not occupied by E2F when transcription increases. On the contrary: the principal mechanism of the effect of E2F, for example, on the regulation of B-myb expression during the cell cycle, is inhibition of expression in the G0 and G1 phases by binding of E2F to its binding site is of the B-myb Gene.

Comparison of the proximal promoter sequence of CDC25C, cyclin A and CDC2 genes with the B-myb promoter showed a distinct similarity not only between the CDEs and E2F binding site but also in the region of the CHRs (FIG. 4). In vitro binding experiments by EMSA with nuclear extracts from HeLa cells indeed show that the B-myb CHR is recognized by nuclear protein(s).

On the basis of these findings, constructs in which the B-myb promoter (Lam et al., EMBO J. 12, 2705 (1993)) was coupled to a luciferase reporter gene (p×P2 vector described by Nordeen, BioTechniques 6, 454, (1988), which is commercially available) were prepared. This construct showed, as described by Lam et al. (1993), an approximately 15-fold repression in quiescent cells when compared with proliferating cells. This repression was virtually completely destroyed (about 2-fold repression) by a mutation of the CHR sequence (TAGGAAAG→TAGGCCTG).

In further experiments, constructs in which the CDC25C promoter was coupled to a luciferase reporter gene were prepared. In addition, in this construct the CHR element of the CDC25C gene was replaced by the CHR element of the B-myb gene (Cdc25C-BmybCHR in FIG. 5). This chimeric construct was no longer cell cycle-regulated. These data prove unambiguously that the B-myb CHR and the CHR of the CDC25C gene are not functionally equivalent, e.g. cannot be exchanged between both nucleotide sequences.

Nucleotide sequences to which repressing transcription factors bind (CHR region) and to which transcription factors of the E2F family bind, such as, for example, the nucleotide sequence CTTGGCGGGAGATAGGAAAGT (SEQ ID NO:5), must therefore be regarded as novel promoter modules which inhibit the transcription of a gene located downstream in the G0 and G1 phases by binding of an E2F transcription factor and a repressing transcription factor.

Priority application, 19605274.2 (Federal Republic of Germany), filed Feb. 13, 1996, including the specification, drawings, claims and abstract, is hereby incorporated by reference.

We claim:

1. A nucleic acid construct comprising:
    a) an activator sequence (element a);
    b) a promoter module (element b) comprising:
        (I) a nucleotide sequence which binds a protein of the E2F family; and
        (ii) a nucleotide sequence that is a cell cycle homology region (CHR); and
    c) a structural gene (element c), wherein element c is not naturally combined with element a and element b.

2. A construct as claimed in claim 1, wherein element a is upstream of element b, which is upstream of element c, and wherein said sequence that binds to a E2F protein is located upstream of said cell cycle homology region.

3. A construct as claimed in claim 1, wherein said structural gene encodes a protein that is expressed in a cell cycle-dependent fashion.

4. A nucleic acid construct as claimed in claim 1, wherein said nucleotide sequence which binds a protein of the E2F family comprises at least one nucleotide sequence which is selected from the group consisting of CTTGGCGGG (SEQ ID NO:1), TTTCGCGCC (SEQ ID NO:2) and TTTCGCGGC (SEQ ID NO:3).

5. A nucleic acid construct as claimed in claim 1, wherein said CHR region comprises the nucleotide sequence TAGGAAA (SEQ ID NO:4).

6. A nucleic acid construct as claimed in claim 1, wherein said promoter module (b) comprises the sequence CTTGGCGGGAGATAGGAAA (SEQ ID NO: 13).

7. A nucleic acid construct as claimed in claim 2, wherein said promoter module (b) interacts with said activator sequence (a), and wherein said interaction affects expression of said gene (c).

8. A nucleic acid construct as claimed in claim 1, wherein said activator sequence is cell-specific.

9. A nucleic acid construct as claimed in claim 1, wherein said activator sequence is virus-specific.

10. A nucleic acid construct as claimed in claim 1, wherein said nucleic acid is DNA.

11. A vector comprising a nucleic acid construct as claimed in claim 1.

12. A vector as claimed in claim 10, wherein said vector is a plasmid vector.

13. A nucleic acid construct as claimed in claim 11, wherein said vector is a viral vector.

14. A nucleic acid construct as claimed in claim 1, wherein said gene (c) encodes a substance which is selected from the group consisting of a cytokine, a growth factor, a cytokine receptor, a growth factor receptor, a protein having an antiproliferative effect, a protein having a cytostatic effect, an antibody, an antibody fragment, an angiogenesis inhibitor, a coagulation factor and an anticoagulant.

15. A nucleic acid construct as claimed in claim 1, wherein said activator sequence (a) is from a promoter that is activated in a cell selected from the group of consisting of an endothelial cell, a smooth muscle cell, a macrophage, a lymphocyte, a leukemia cell, a tumor cell and a glial cell.

16. A nucleic acid construct as claimed in claim 1, wherein said activator sequence (a) is a promoter or enhancer sequence from a virus, wherein said virus is selected from the group consisting of the viruses HBV, HCV, HSV, HPV, EBV, HTLV, CMV, SV40 and HIV.

17. A nucleic acid construct as claimed in claim 1, wherein said gene (c) encodes an enzyme which cleaves a precursor of a pharmaceutical to produce a pharmaceutical.

18. An isolated cell which comprises a nucleic acid construct as claimed in claim 1.

19. A nucleic acid construct as claimed in claim 1, wherein said activator sequence is metabolic-specific.

* * * * *